(12) United States Patent
Günther et al.

(10) Patent No.: US 12,127,779 B2
(45) Date of Patent: Oct. 29, 2024

(54) METHODS, SYSTEMS, AND APPARATUSES FOR TISSUE ABLATION USING A MODULATED EXPONENTIAL DECAY PULSE

(71) Applicant: Inter Science GmbH, Gisikon (CH)

(72) Inventors: Enric Günther, Hattersheim (DE); Boris Rubinsky, El Cerrito, CA (US); Nina Klein, Friedrichsdorf (DE); Paul Mikus, Mission Viejo, CA (US); Michael Stehling, Rödermark (DE)

(73) Assignee: Inter Science GmbH, Gisikon (CH)

( * ) Notice: Subject to any disclaimer, the term of this patent is extended or adjusted under 35 U.S.C. 154(b) by 766 days.

(21) Appl. No.: 17/273,302

(22) PCT Filed: Sep. 4, 2019

(86) PCT No.: PCT/US2019/049588
§ 371 (c)(1),
(2) Date: Mar. 3, 2021

(87) PCT Pub. No.: WO2020/051241
PCT Pub. Date: Mar. 12, 2020

(65) Prior Publication Data
US 2021/0330371 A1    Oct. 28, 2021

Related U.S. Application Data

(60) Provisional application No. 62/726,896, filed on Sep. 4, 2018.

(51) Int. Cl.
*A61B 18/12* (2006.01)
*A61B 18/00* (2006.01)

(52) U.S. Cl.
CPC ............ *A61B 18/1206* (2013.01); *A61B 2018/00577* (2013.01); *A61B 2018/00613* (2013.01);
(Continued)

(58) Field of Classification Search
CPC ...... A61B 18/1206; A61B 2018/00577; A61B 2018/00613; A61B 2018/00702;
(Continued)

(56) References Cited

U.S. PATENT DOCUMENTS 5,389,069 A    2/1995  Weaver et al.
5,468,223 A    11/1995 Mir
(Continued)

FOREIGN PATENT DOCUMENTS

EP    2311522 A1    4/2011
EP    2425871 A2    3/2012
(Continued)

OTHER PUBLICATIONS

International Search Report and Written Opinion for International Application No. PCT/US2019/049588, mailed Nov. 29, 2019.
(Continued)

*Primary Examiner* — Michael F Peffley
(74) *Attorney, Agent, or Firm* — Stoel Rives LLP

(57) ABSTRACT

Example methods and apparatuses are disclosed for providing tissue ablation through electrolysis, electroporation, or a combination thereof. A pulse that has an element of decay may be applied to a target for tissue ablation while the decay is modulated. In some examples, apparatus including a controller and switches may be used to modulate the decay and/or selectively apply the pulse to the target. The apparatus may further include resistors and/or other elements to modulate a magnitude of the pulse and/or a slope of a decay of the pulse.

20 Claims, 27 Drawing Sheets

(52) U.S. Cl.
CPC .............. *A61B 2018/0072* (2013.01); *A61B 2018/00767* (2013.01); *A61B 2018/00791* (2013.01); *A61B 2018/00827* (2013.01); *A61B 2018/00875* (2013.01); *A61B 2018/00892* (2013.01); *A61B 2018/1246* (2013.01)

(58) Field of Classification Search
CPC .. A61B 2018/0072; A61B 2018/00767; A61B 2018/00791; A61B 2018/00827; A61B 2018/00875; A61B 2018/00892; A61B 2018/1246; A61N 1/325; A61N 1/327
See application file for complete search history.

(56) References Cited

U.S. PATENT DOCUMENTS

| | | |
|---|---|---|
| 5,911,223 A | 6/1999 | Weaver et al. |
| 6,300,108 B1 | 10/2001 | Rubinsky et al. |
| 6,366,808 B1 | 4/2002 | Schroeppel et al. |
| 6,403,348 B1 | 6/2002 | Rubinsky et al. |
| 6,767,347 B2 | 7/2004 | Sharkey et al. |
| 7,113,821 B1 | 9/2006 | Sun et al. |
| 7,344,533 B2 | 3/2008 | Pearson et al. |
| 7,680,543 B2 | 3/2010 | Azure |
| 7,718,409 B2 | 5/2010 | Rubinsky et al. |
| 7,955,827 B2 | 6/2011 | Rubinsky et al. |
| 8,048,067 B2 | 11/2011 | Davalos et al. |
| 8,145,316 B2 | 3/2012 | Deem et al. |
| 8,282,631 B2 | 10/2012 | Davalos et al. |
| 8,849,413 B2 | 9/2014 | Makdissi |
| 8,926,606 B2 | 1/2015 | Davalos et al. |
| 9,005,189 B2 | 4/2015 | Davalos et al. |
| 9,283,051 B2 | 3/2016 | Garcia et al. |
| 9,700,368 B2 | 7/2017 | Callas et al. |
| 9,901,735 B1 | 2/2018 | Lee et al. |
| 10,154,873 B2 | 12/2018 | Rubinsky et al. |
| 10,390,874 B2 * | 8/2019 | Rubinsky .................. C25B 1/26 |
| 10,939,949 B2 | 3/2021 | Rubinsky et al. |
| 11,123,475 B2 | 9/2021 | Rubinsky et al. |
| 11,260,165 B2 | 3/2022 | Rubinsky et al. |
| 11,857,244 B2 | 1/2024 | Rubinsky et al. |
| 11,866,833 B2 | 1/2024 | Rubinsky et al. |
| 2001/0021868 A1 | 9/2001 | Herbst et al. |
| 2002/0010491 A1 | 1/2002 | Schoenbach et al. |
| 2002/0143365 A1 * | 10/2002 | Herbst ................. A61N 1/0428 607/2 |
| 2003/0042134 A1 | 3/2003 | Tremblay et al. |
| 2004/0213698 A1 | 10/2004 | Tennakoon et al. |
| 2006/0116663 A1 | 6/2006 | Joshi et al. |
| 2006/0293731 A1 | 12/2006 | Rubinsky et al. |
| 2008/0167650 A1 | 7/2008 | Joshi et al. |
| 2009/0287208 A1 | 11/2009 | Rosemberg |
| 2010/0030211 A1 | 2/2010 | Davalos et al. |
| 2010/0036446 A9 | 2/2010 | Auge et al. |
| 2010/0168646 A1 | 7/2010 | Greenbaum et al. |
| 2010/0183745 A1 | 7/2010 | Rossi et al. |
| 2011/0106072 A1 | 5/2011 | Sundquist et al. |
| 2012/0059255 A1 | 3/2012 | Paul et al. |
| 2012/0071874 A1 | 3/2012 | Davalos et al. |
| 2012/0130369 A1 | 5/2012 | Cadossi et al. |
| 2012/0150173 A1 | 6/2012 | Joshi et al. |
| 2012/0220998 A1 | 8/2012 | Long et al. |
| 2013/0218157 A1 | 8/2013 | Callas et al. |
| 2014/0066913 A1 | 3/2014 | Sherman |
| 2014/0276767 A1 * | 9/2014 | Brotz .................. A61B 18/1206 606/34 |
| 2014/0316485 A1 | 10/2014 | Ackermann et al. |
| 2016/0184003 A1 * | 6/2016 | Srimathveeravalli ........................ A61B 18/1233 606/39 |
| 2016/0287867 A1 | 10/2016 | Rubinsky et al. |
| 2016/0296269 A1 | 10/2016 | Rubinsky et al. |
| 2018/0193082 A1 * | 7/2018 | Rubinsky ........... A61B 18/1402 |
| 2019/0117291 A1 | 4/2019 | Rubinsky et al. |
| 2019/0357960 A1 | 11/2019 | Rubinsky et al. |
| 2021/0186592 A1 | 6/2021 | Rubinsky et al. |
| 2021/0220532 A1 | 7/2021 | Rubinsky et al. |
| 2022/0105256 A1 | 4/2022 | Rubinsky et al. |
| 2022/0210525 A1 | 4/2022 | Rubinsky et al. |
| 2024/0065749 A1 | 2/2024 | Rubinsky et al. |

FOREIGN PATENT DOCUMENTS

| | | |
|---|---|---|
| EP | 1696812 B1 | 7/2015 |
| WO | 03103521 A1 | 12/2003 |
| WO | 2007070637 A2 | 6/2007 |
| WO | 2015021113 A1 | 2/2015 |
| WO | 2015073877 A1 | 5/2015 |
| WO | 2015073885 A1 | 5/2015 |
| WO | 2016178697 A1 | 11/2016 |
| WO | 2020051241 A1 | 3/2020 |

OTHER PUBLICATIONS

Klein et al., "The combination of electroportation and electrolysis (E2) employing different electrode arrays for ablation of large tissue volumes", (2019) PLoS ONE 14(8):e0221393.https://doi.org/10.1371/journal.pone.0221393.

Czymek, R. et al., "Electrochemical treatment. An investigation of dose-response relationships using an isolated liver perfusion model", Saudi journal of gastroenterology : official journal of the Saudi Gastroenterology Association (2011). doi: 10.4103/1319-3767.84491.

Davalos, R. V. et al., "Tissue Ablation with Irreversible Electroporation", Ann Biomed Eng (2005). doi: 10.1007/s10439-005-8981-8.

Edd, J. F. et al., "In vivo results of a new focal tissue ablation technique. Irreversible electroporation", IEEE transactions on biomedical engineering (2006). doi: 10.1109/TBME.2006.873745.

Fosh, B. G. et al., "Electrolytic ablation of the rat pancreas. A feasibility trial", BMC Gastroenterol (2001). doi: 10.1186/1471-230X-1-9.

Gravante, G. et al., "Experimental application of electrolysis in the treatment of liver and pancreatic tumours. Principles, preclinical and clinical observations and future perspectives", Surgical oncology (2011). doi: 10.1016/j.suronc.2009.12.002.

Guenther, E. et al., "Electrical breakdown in tissue electroporation", Biochemical and biophysical research communications (2015). doi: 10.1016/j.bbrc.2015.10.072.

Horwitz, E. M. et al., "Definitions of biochemical failure that best predict clinical failure in patients with prostate cancer treated with external beam radiation alone. A multi-institutional pooled analysis", The Journal of urology (2005). doi: 10.1097/01.ju.0000152556.53602.64.

Klein, N. et al., "Single exponential decay waveform; a synergistic combination of electroporation and electrolysis (E2) for tissue ablation", PeerJ (2017). doi: 10.7717/peerj.3190.

Lloyd, M et al., "Electrolysis—a new method of renal ablation?", BJU international (2012). doi: 10.1111/j.1464-410X.2012.11478.x.

MacLaren, J. S. et al., "Electrolysis in Prostate Enlargement", Ann. Surg.(9), 347-350 (1989).

Martin, R. C. et al., "Intra-operative Anesthesia Management in Patients Undergoing Surgical Irreversible Electroporation of the Pancreas, Liver, Kidney, and Retroperitoneal Tumors", Anesthesiology and pain medicine (2015). doi: 10.5812/aapm.22786.

Mir, L. M. et al., "The basis of electrochemotherapy", Methods in molecular medicine (2000). doi: 10.1385/1-59259-080-2:99.

Neumann, E. et al., "Electroporation and electrofusion in cell biology", Plenum Press, New York (1989).

Neumann, E. et al., "Gene transfer into mouse lyoma cells by electroporation in high electric fields", The EMBO journal 1(7), 841-845 (1982).

Onik, G. et al., "Irreversible Electroporation: First Patient Experience Focal Therapy of Prostate Cancer", In: Rubinsky, B. (ed.) Irreversible Electroporation. Series in Biomedical Engineering, pp. 235-247. Springer-Verlag Berlin Heidelberg, Berlin, Heidelberg (2010).

(56) References Cited

OTHER PUBLICATIONS

Phillips, M. et al., "Combining Electrolysis and Electroporation for Tissue Ablation", Technology in cancer research & treatment (2015). doi: 10.1177/1533034614560102.

Phillips, M. et al., "Modulating electrolytic tissue ablation with reversible electroporation pulses", Technology (2015). doi: 10.1142/S233954781550003X.

Phillips, M. et al., "Tissue Ablation by a Synergistic Combination of Electroporation and Electrolysis Delivered by a Single Pulse", Annals of biomedical engineering (2016). doi: 10.1007/s10439-016-1624-4.

Robertson, G. S. et al., "Experimental study of electrolysis-induced hepatic necrosis", The British journal of surgery (1998). doi: 10.1046/j.1365-2168.1998.00806.x.

Rubinsky, B. et al., "Irreversible electroporation. A new ablation modality—clinical implications", Technology in cancer research & treatment (2007). doi: 10.1177/153303460700600106.

Rubinsky, B. et al., "Minimally Invasive, Non-Thermal Tissue Ablation with a Single Exponential Decay Electrolytic Electroporation Waveform", JTMR (2016). doi: 10.21614/jtmr-21-4-98.

Rubinsky, L. et al., "Electrolytic Effects During Tissue Ablation by Electroporation", Technology in cancer research & treatment (2016). doi: 10.1177/1533034615601549.

Scheffer, H. J. et al., "Irreversible Electroporation for Colorectal Liver Metastases", Techniques in vascular and interventional radiology (2015). doi: 10.1053/j.tvir.2015.06.007.

Stehling, M. K., "Combination of Electrolysis and Electroporation for Tissue Ablation", PloS one (2016). doi: 10.1371/journal.pone.0148317.

Tasu, J. P. et al., "Irreversible Electroporation for Locally Advanced Pancreatic Cancer. Where Do We Stand in 2017?", Pancreas (2017). doi: 10.1097/MPA.0000000000000793.

Weaver, J. C. et al., "Theory of electroporation. A review", Bioelectrochemistry and Bioenergetics (1996). doi: 10.1016/S0302-4598(96)05062-3.

Extended European Search Report dated Apr. 13, 2022 for EP Application 19857135.8, pp. 1-8.

Ivorra, et al., "Electric Field Modulation in Tissue Electroporation With Electrolytic and Non-Electrolytic Additives", Bioelectrochemistry 70, Feb. 2007, pp. 551-560.

Ivorra, et al., "In Vivo Electrical Impedance Measurements During and After Electroporation of Rat Liver", Bioelectrochemistry 70, Oct. 2006, pp. 287-295.

Lluis, Mir M, et al., "Mechanisms of Electorochemotherapy", Advanced Drug Delivery Reviews vol. 35, No. 1, DOI: 10.1016/S0169-409X(98)00066-0, Jan. 4, 1999, pp. 107-118.

Lv, Yanpeng, et al., "Molecular and histological study on the effects of electrolytic electroporation on the liver", Bioelectrochemistry vol. 125, 2019, pp. 79-89.

U.S. Appl. No. 18/527,155 titled "Methods, Systems, and Apparatuses for Tissue Ablation Using Electrolysis Andpermeabilization" filed Dec. 1, 2023.

Denet, Anne-Rose, et al., "Transdermal delivery of timolol by electroporation through human skin", Journal of Controlled Release, Elsevier, Amsterdam, NL, vol. 88, No. 2, Doi: 10.1016/S0168-3659(03)00010-5, Mar. 7, 2003, pp. 253-262.

Saulis, Gintautas, et al., "Changes of the solution pH due to exposure by high-voltage electric pules", Bioelectrochemistry, Elesevier, Amsterdam, NL, vol. 67, No. 1, Sep. 1, 2005, pp. 101-108.

\* cited by examiner

A  B  C

G  H  I

D  E  F

J  K  L

A

B

C

D

E

F

G

H

METHODS, SYSTEMS, AND APPARATUSES FOR TISSUE ABLATION USING A MODULATED EXPONENTIAL DECAY PULSE

CROSS-REFERENCE TO RELATED APPLICATION(S)

This application is a U.S. national stage application of PCT Application No. PCT/US2019/049588 filed Sep. 4, 2019, which claims priority to U.S. Provisional Application No. 62/726,896 filed Sep. 4, 2018, the contents of which are incorporated herein by reference, in their entirety, for any purpose.

BACKGROUND

Electrolysis has been used for minimally invasive tissue ablation since the early 1800's. The process of electrolysis occurs at the electrode surfaces for electrodes submerged in an ionic conducting media. New chemical species are generated at the interface of the electrodes as a result of the electric potential driven transfer between electrons and ions or atoms. The various chemical species produced near the electrodes diffuse away in a process driven by differences in electrochemical potential. In physiological solutions these chemical reactions also yield changes in pH, resulting in an acidic region near the anode and a basic region near the cathode. Tissue ablation is driven by two factors: a cytotoxic environment developing due to local changes in pH, as well as the presence of some of the new chemical species formed during electrolysis. Electrolysis is a chemical ablation mechanism, and the extent of ablation is a function of the concentration of the chemical species and the exposure time to these chemicals. The total amount of electrolytic products generated during electrolysis is related to the charge delivered during the process, and therefore the total charge is used as a quantitative measure for the extent of electrolysis.

Over the last two decades, substantial research has been done on tissue ablation by electrolysis, including cell and animal experiments, mathematical modeling, and clinical work. In the contemporary literature, electrolytic ablation is sometimes referred to as Electro-Chemical Therapy (EChT). Electrolytic ablation has been shown to exhibit several unique attributes. First, due to the chemical nature of the ablation process, the diffusion of chemical species in the tissue and the rate of chemical reactions dominate the time scale of the procedure. Second, the chemical products at the anode differ from those formed at the cathode, thus resulting in distinct mechanisms of ablation Finally, electro-osmotic forces drive the migration of water from the anode to the cathode, further magnifying the contrasting physiological effects at the electrode surfaces. From an operational standpoint, electrolysis may use very low voltages and currents, providing advantages relative to other ablation techniques, e.g. reduced instrumentation complexity. It is, however, a lengthy procedure, controlled by the process of diffusion and the need for high concentrations of electrolytically-produced ablative chemical species.

Electroporation also harnesses an electricity-induced phenomenon; it differs from electrolysis by employing a different set of biophysical principles. The bioelectric phenomenon of electroporation is characterized by the permeabilization of the cell membrane through the application of very brief, high-magnitude electric field pulses. The extent of membrane permeabilization is a function of the electric field strength. Electroporation can be used to produce reversible pores in the lipid bilayer, allowing for the introduction of molecules such as genes and drugs into cells. The electric parameters, however, can be designed to produce irreversible defects, resulting in a cell membrane that does not reseal after the field is removed. Reversible electroporation techniques have been combined with anticancer drugs such as bleomycin to target cancerous tissues for successful clinical use in the field of electrochemotherapy. Reversible electroporation is also used in other medical and biotechnological applications, including transfection and introduction of molecules such as siRNA into cells that survive the permeabilization process. Electroporation specifically targets the cell membrane through the application of an electric field that develops instantaneously.

SUMMARY

Systems and methods are disclosed for providing controlled delivery of electrolysis treatment and cellular permeabilization treatment to a site in tissue via modulated waveforms (e.g., a decay pulse where the decay is modulated). A system may include a power supply, a capacitor bank, an electrode and a controller unit. In some examples, the power supply may be a capacitor bank. In some examples, the electrode may be an electrode array. A controller may control a charge applied to the electrode(s) to induce a direct current through the tissue to produce electrolysis and a voltage to produce electropermeabilization. A modulated waveform may include modulation, variation and combination of voltage, duration, frequency, charge, polarity and shape of a waveform or multiple waveforms, energy path selection and number of waveforms applied between one electrode or a composition of electrodes.

An example system according to principles of the present disclosure may include a waveform generator configured to generate a waveform comprising at least one of a voltage or a current, a controller configured to modulate the waveform generated by the waveform generator to cause electroporation and electrolysis at an ablation target, and at least one electrode electrically coupled to the waveform generator and configured to receive the modulated waveform and deliver the energy (e.g., at least one of the voltage or the current) to the ablation target.

An example method according to principles of the present disclosure may include applying a pulse of at least one of a voltage or a current to an ablation target, wherein the pulse is configured to cause electroporation and electrolysis at the ablation target and modulating the pulse to intermittently interrupt the at least one of the voltage or the current at the ablation target. This may stretch the energy delivery duration and reduce the energy delivery density per unit time in a controllable fashion.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which

DETAILED DESCRIPTION

Figure 1:
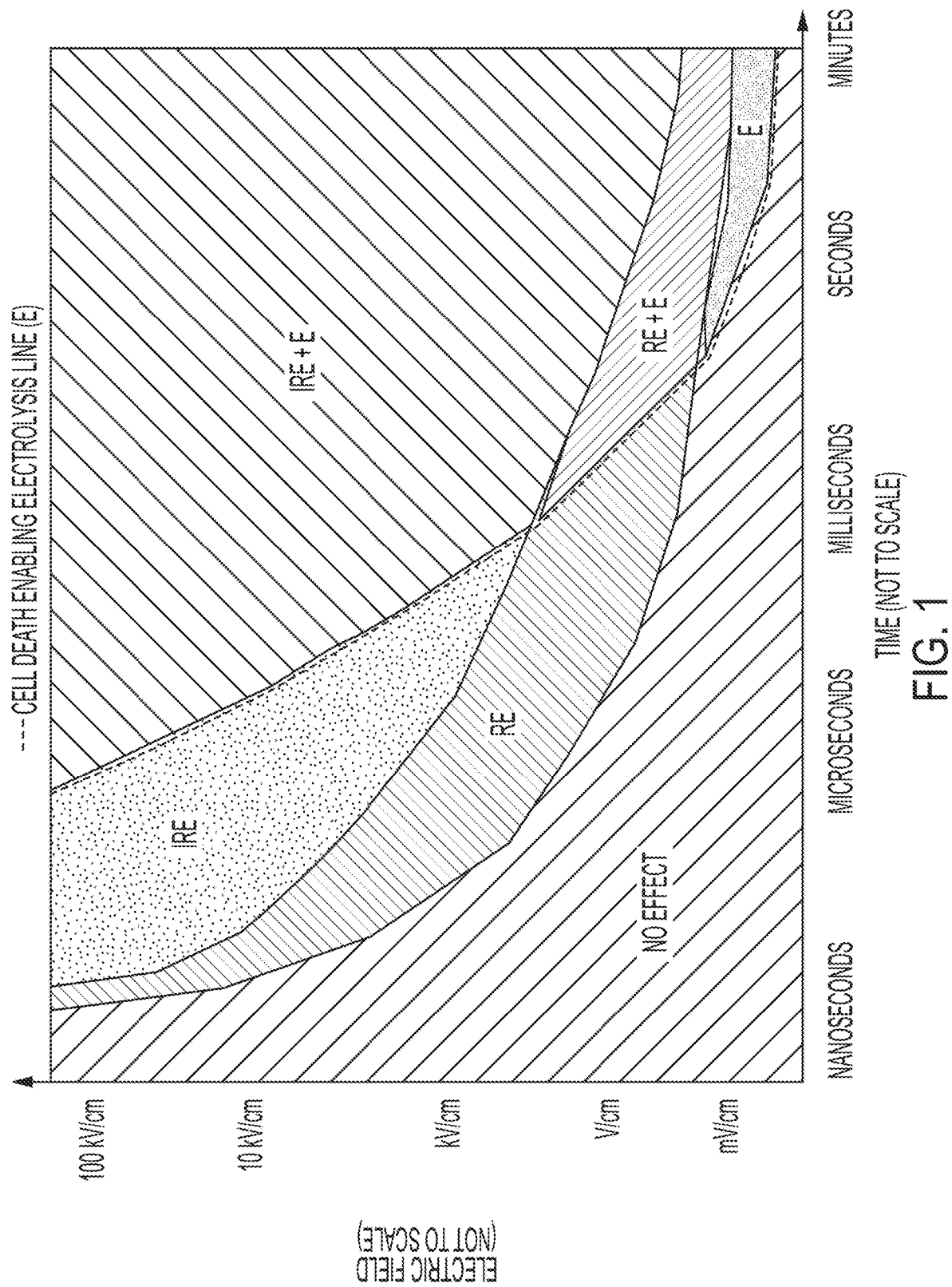
FIG. 1 is a schematic illustration of various domains for electroporation and electrolysis, with respect to their effect on tissue and cell ablation.

Certain details are set forth below to provide a sufficient understanding of embodiments of the disclosure. However, it will be clear to one skilled in the art that embodiments of the disclosure may be practiced without these particular details. Moreover, the particular embodiments of the present disclosure described herein are provided by way of example and should not be used to limit the scope of the invention to these particular embodiments. In other instances, well-known materials, components, processes, controller components, software, circuitry, timing diagrams, and/or anatomy have not been described or shown in detail in order to avoid unnecessarily obscuring the embodiments.

Tissue ablation by minimally invasive applications has various medical uses. Many minimally invasive tissue ablation techniques employ electricity. The effects used can be classified into thermal and non-thermal applications. The thermal modalities use temperature elevation by means of dissipation of electrical energy (Joule heating effect), or temperature decrease to freeze the treated tissue. Various electromagnetic frequencies are used for thermal tissue ablation, including radio frequency, microwave frequency and direct current. Electrolysis and various modes of electroporation rely on non-thermal mechanisms of tissue ablation, where they affect only the cells within tissue, sparing the extracellular matrix and other organ structures. Several applications are advantageous for non-thermal ablation, in particular treatment of tumors which are in high proximity to sensitive sites.

In electrolytic ablation, electric currents are delivered through two electrodes which encompass the targeted tissue. The current is delivered in such a way as to produce electrolysis at the surface of electrodes submerged in tissue, which is an ionic conducting media. New chemical species (e.g., hypochlorous acid (HClO)) are generated at the interface of the electrodes and diffuse away from the electrodes into the tissue. This diffusion occurs along a concentration gradient and by electrophoresis. These species are able to create a cytotoxic environment which can induce cell death. A leading mechanism of cell death is due to local changes in pH, however, other mechanisms may also be at play. Electrolytic ablation requires very low voltage and current, providing advantages relative to other ablation techniques, including reduced apparatus complexity. However, the ablation caused by electrolysis needs high electrolytic species concentration and consequently long treatment duration (tens of minutes to hours), which is a drawback. Additionally, the long treatment time facilitates normal, non-Nernst-Planck type diffusion and blood transportation phenomenon. This can lead to an almost unpredictable distribution of electrolytic products and therefore difficult predictability of ablation dimensions.

Electroporation is the permeabilization of the cell membrane by pulsed electric field delivered across the cell. The effect on the cell membrane is a function of the electric field strength and pulse time duration. Lower electric fields produce reversible electroporation, in which case the cell returns to its original state a few seconds or minutes after the electric field has ceased. This phenomenon is used for gene delivery, uptake of drugs or genetic material into cells, inserting proteins into the cell membrane, and fusing between individual cells. Electrochemotherapy, the combination of reversible electroporation and chemotherapeutical drugs, such as bleomycin, has been used successfully for tumor ablation in clinical settings. Electrochemotherapy usually utilizes eight 100 microsecond long pulses, with electric fields of between 200-500 V/cm (1000-1500 V/cm voltage to needle type electrode distance ratio). While the application is effective at cancer treatment, it requires the application of drugs, putting it into the regulatory domain of drug therapies.

A combination of higher electric fields and longer exposure time of these electroporation pulses results in cell death through a mechanism broadly referred to as irreversible electroporation (IRE), i.e. the cells succumb to the membrane permeabilization by electroporation. IRE has gained success in clinical tumor ablation. IRE can ablate tissues without the need for drug injection and without resorting to thermal damage. This is why the procedure is also known as non-thermal irreversible electroporation (NTIRE). The NTIRE procedure is much faster than conventional electrolytic ablation, and preserves sensitive structures. However, the procedure employs very high electric fields in the order of 500-1000 V/cm (1500 to 3000 V/cm voltage to needle type electrode distance ratio) and sometimes hundreds of pulses over minutes with strict limitations on distance and parallelism of electrodes. The use of high electric fields and the large number of pulses used in NTIRE has disadvantages. NTIRE pulses induce muscle contractions that require the use of a muscle relaxant and deep anesthesia during surgery. The muscle contractions may also move the electrodes during treatment, resulting in possible complications. This is particularly detrimental when hundreds of pulses are delivered. Additionally, the high fields almost inevitably produce a high amount of electrolytic products and spark plasma (after some pulses) causing a pressure wave (referred to as discharges or sparks or arcing) with loud acoustic manifestation and mechanical tissue damage. An example numerical value for electric fields that develop across a gas layer to generate an electric breakdown and the consequent sparks may be approximately 30 kV/cm in some applications. Technically, even if stopped in time, they can cause low-impedance situations which will cause machine failures and with that a risk for the patient. In addition, while the actual electroporation part of the procedure is brief, the logistic complications associated with the placement of the electrodes and the large number of pulses substantially lengthen the procedure.

Electrolytic electroporation (E2) ablation technology, the combination of electrolysis and electroporation, disclosed herein was developed in a systematic way, from basic concept through small animal studies to large animal studies. E2 may provide a minimally invasive tissue ablation technology with potential advantages over tissue ablation by either electroporation or electrolysis alone. One potential advantage is that E2 requires substantially fewer electric pulses and at a lower electric field than conventional NTIRE. The latter is the main reason for most of the challenges of IRE in terms of treatment design, maximum ablation size per electrode placement and electrical safety design. E2 is also non-thermal and does not require the injection of drugs, unlike Electrochemotherapy, which requires the injection of bleomycin or other agents. Without being bound to a particular theory, a mechanistic explanation of the E2 technology may be related to the permeabilization of the cell membrane by all modes of electroporation and nano pulses. The products of electrolysis may, thereby, gain access to the interior of the cell by the electroporation permeabilized cell membrane (homeostasis impairment), and cause cell death at a much lower dose than that required for tissue ablation by conventional electrolysis.

Some studies on E2 have employed waveforms that delivered electrolysis and electroporation sequentially and separately. This remains a possible E2 modality as it may require only the addition of a low voltage electrolysis device to conventional electroporation pulses. The disadvantage to this approach may be that it could require the use of two devices and two control systems. Subsequently, some studies have shown that the combination electroporation and electrolysis can be achieved through the design of an E2 waveform that delivers simultaneously electroporation and electrolysis. A potential waveform for this has some resemblance to an exponential decay waveform.

As described herein, a modulated E2 waveform according to the principles of the present disclosure may produce better and safer results than when the energy is delivered in a fast and/or non-modulated E2 waveform. In some embodiments, the modulated waveforms described herein may prolongs and/or increases the electrolysis-delivering tail of the exponential decay-like waveform. In some embodiments, this may be achieved by discharging several capacitors either sequentially or simultaneously in a controlled manner Key control parameters may include the voltage at the onset of the waveform, the electrical charge delivered as well as the periods and/or total time of the discharge. In the modulated E2 waveform, a part of the waveform may be designed to induce cell membrane permeabilization without plasma formation, while another part generates the electrolytic products. The trailing lower voltage of the modulated waveform may provide an electrophoretic force to transport the electrolytic products from electrodes through a treated zone (e.g., tissue). In some embodiments, the modulated waveforms may be adjusted as desired to achieve different results, such as avoidance of discharge, inducing controlled discharge, tissue-dependent cell death, cell-dependent cell death, Joule heating, time-dependent effects of cell death and/or aiming to produce particular toxic substances during the procedure that will target specific tissue and/or cells.

FIG. 1 is a schematic illustration of various domains for electroporation and electrolysis. The illustration shown in FIG. 1 is given as electric field strength versus time. While FIG. 1 is provided as an example of a typical curve, its characteristics (e.g., slope) may change with cell type. The values given on the axis are typical to mammalian cells. The time range for irreversible electroporation may be from nanoseconds to minutes and the voltage range may be from several hundred V/cm (200 V/cm) to 100 V/cm. For reversible electroporation that voltage range may be from 50 V/cm to several hundred V/cm (500 V/cm) and the time range may also be from nanoseconds to several minutes. Electrolysis may occur when current flows from electrodes to tissue (electrons to and from ions) and/or when the voltage exceeds a certain threshold prescribed by the electrochemical potential of the electrodes in relation to the solution. This threshold value may depend on the electrode material, composition of the solution, pH, and/or temperature. Typical values may be several volts, for example from 0.01 V to 10 V. In FIG. 1, the curve that displays values in which electrolysis products cause cell death may include multiple regions. That curve may include regions in which cell death may be caused by electrolysis alone, by combination of reversible electroporation and electrolysis, and/or combination of irreversible electroporation and electrolysis.

The diagram illustrated in FIG. 1 is schematic. However, it illustrates that the minimal time of exposure required for cell death with involvement of electrolysis may increase in the following order: a) combination used from irreversible electroporation with electrolysis to b) reversible electroporation with electrolysis to c) electrolysis alone. As shown in FIG. 1, the electrolytic involvement cell death curve may only have a lower limit, since electrolysis may occur in the presence of a process that involves transfer of electrons to ions, but may not always cause cell death. Typical times for IRE+E are single microseconds (e.g., approximately 0.1 microsecond-1 microsecond) and for RE+E are several tens of microseconds (e.g., 10 microseconds) and for E are seconds (e.g., 1 sec).

For a given electric field strength, the electric field applied for over a threshold time may generate sufficient electrolysis to enable cell death to occur. The threshold amount of time required may vary based on the electric field strength used. Accordingly, as seen in FIG. 1, there may be at least five domains—a region of reversible electroporation only (RE), a region of irreversible electroporation (IRE) only, a region of reversible electroporation plus electrolysis (RE+E), a region of irreversible electroporation plus electrolysis (IRE+E), and a region of electrolysis without electroporation (E). As used herein, the regions of IRE+E and RE+E are referred to as E2. Tissue ablation may be performed using the desired techniques (e.g. IRE, RE, E, IRE+E, or RE+E) by selecting a field strength and time associated with the domain of interest.

Figure 2:
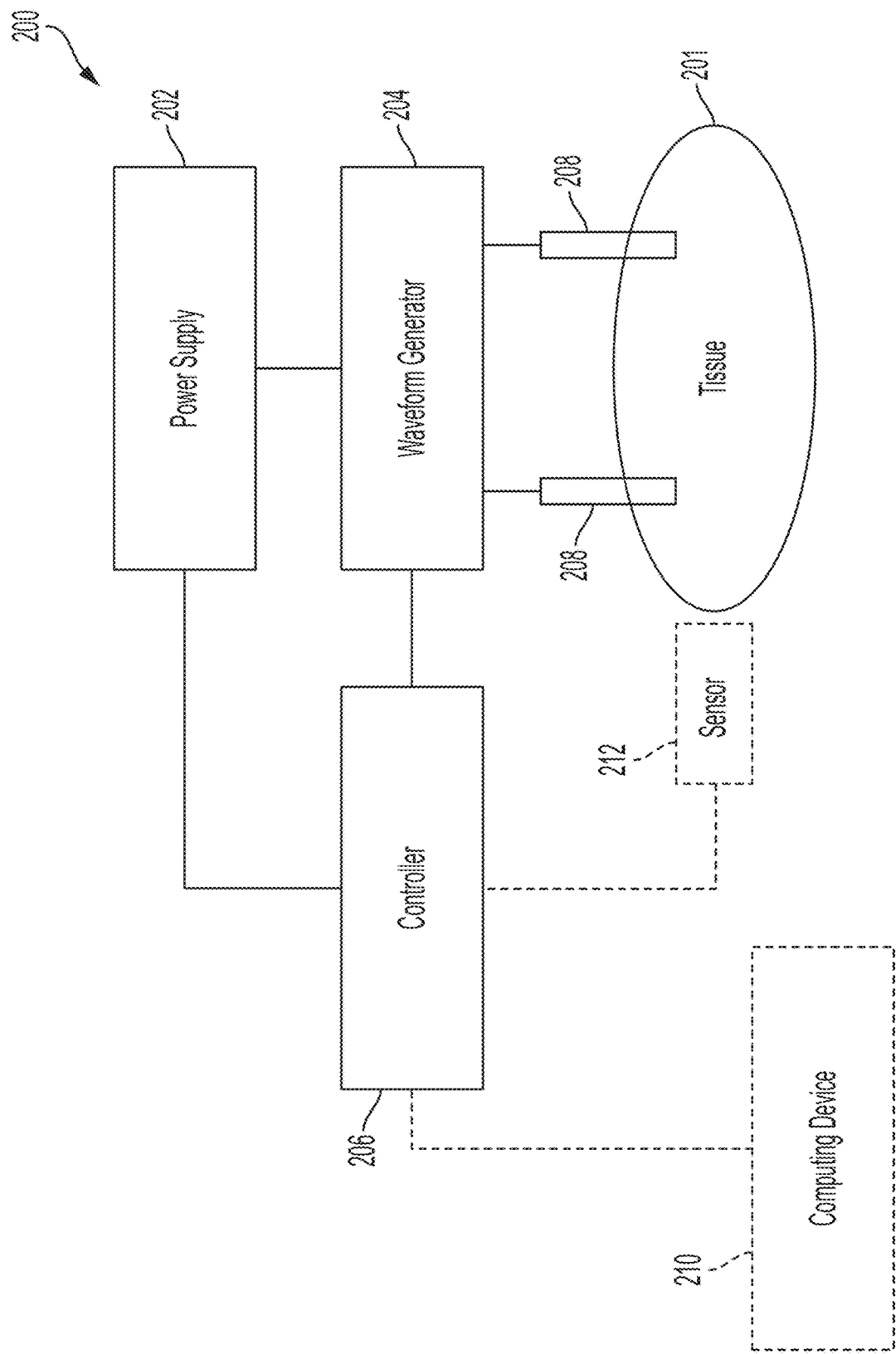
FIG. 2 is a block diagram of a system for delivering electrolytic electroporation according to an embodiment of the disclosure.

FIG. 2 is a block diagram of a system 200 for delivering electrolytic electroporation (E2) according to principles of the present disclosure. In some embodiments, the system 200 may include a power supply 202, a waveform generator 204, a controller 206, and one or more electrodes 208. For context, an ablation target is also shown. In the example in FIG. 2, tissue 201 is the ablation target.

The power supply 202 may provide a current and/or voltage to the waveform generator 204 and/or controller 206. In some embodiments, the power supply 202 may not be directly coupled to the waveform generator 204 and power is supplied from the power supply 202 to the waveform generator 204 via the controller 206. In some embodiments, the controller 206 may selectively couple and decouple the power supply 202 from the waveform generator 204. In some embodiments, a capacitor array can be part of the waveform generator 204 or be serial with the power supply 202 and the waveform generator 204

The waveform generator 204 may generate a waveform having voltage and/or current characteristics suitable for delivering E2. In some examples, the waveform may have a high voltage phase suitable for delivering electroporation and a low voltage phase suitable for delivering electrolysis. In some embodiments, the waveform provided by the waveform generator 204 may be a pulse that has an initial voltage and/or current which decays over time. In some examples, the decay may be an exponential decay. As will be described in more detail with reference to FIG. 4, the waveform generator 204 may include one or more capacitors and/or one or more resistors suitable for generating the pulse.

The controller 206 may control the timing, strength, duration, rate of decay, polarity, and/or otherwise modulate the waveform generated by the waveform generator 204. In some embodiments, the controller 206 may control the coupling of the waveform generator 204 to the power supply 202 and/or the one or more electrodes 208. In some embodiments, as will be described in more detail with reference to FIGS. 3 and 4, the controller 206 may modulate the waveform by controlling one or more switches coupling a capacitor of the waveform generator 204 to the one or more electrodes 208.

In some embodiments, the controller 206 may include a programmable chip. In some embodiments, the controller 206 may be programmed or otherwise controlled by a computing device 210 that includes one or more processors. The controller 206 may be coupled by a wire or communicate with the computing device 210 wirelessly. The computing device 210 may be implemented using, for example, a desktop, laptop, server, handheld device, a personal computer, a tablet computer, and/or a smart phone. In some examples, the computing device 210 may be integrated with and/or shared with another piece of medical equipment. In some embodiments, the controller 206 may be implemented using a computing device or include computing device 210. In some embodiments, the controller 206 may be remotely coupled to the waveform generator 204 and/or power supply 202. The controller 206 may be coupled by a wire or communicate with the waveform generator 204 and/or power supply 202 wirelessly.

In some embodiments, the system 200 may further include one or more sensors 212. The sensors 212 may be communicatively coupled to the controller 206 in some embodiments and placed in, on, and/or near the tissue 201. The sensors 212 may collect data on parameters such as voltage, current, impedance, and/or temperature within the tissue. In some embodiments, the sensors 212 may be implemented by an imaging system such as infrared, ultrasound, light, magnetic resonance imaging, impedance tomography and/or any x-ray based imaging. The imaging system may image the tissue 201. The data and/or images acquired by the sensors 212 may be used by the controller 206 to modulate the waveform of the waveform generator 204 in some embodiments. For example, the controller 206 may reduce a voltage of the waveform responsive to a voltage, temperature, and/or temperature detected by the sensor 212 exceeding a threshold value.

Although shown as separate components, the power supply 202, waveform generator 204, and/or controller 206 may be included in a same device and/or otherwise integrated into fewer components. In some embodiments, the computing device 210 and/or sensor 212 may be incorporated with the power supply 202, waveform generator 204 and/or controller 206.

The one or more electrodes 208 may be coupled to the waveform generator 204 and configured to provide the waveform to the tissue 201. In the example shown in FIG. 2, system 200 includes two electrodes 208. However, the system 200 may include more or fewer electrodes in other embodiments. For example, system 200 may include a single electrode 208 and an element for providing a remote connection to ground. In other embodiments, the system 200 may include several electrodes (e.g., circular, array). The electrodes 208 may be implemented by any known or future electrodes. For example, needle electrodes, catheter electrodes, and/or needle patch electrodes. Furthermore, although the electrodes 208 are depicted as permeating the tissue 201, in other embodiments, the electrodes 208 may be on a surface of the tissue 201 and/or within a cavity of the tissue 201.

As discussed previously, a waveform for delivering E2 to an ablation target may be a pulse of a voltage and/or current with an element of decay. For example, the waveform may resemble the discharge of a capacitor. According to principles of the present disclosure, the waveform may be modulated to alter the rate of decay, polarity, and/or the timing of delivery of the voltage and/or current of the waveform to an ablation target. For example, in some embodiments, the waveform may be modulated by decoupling a capacitor from a conductive path such that discharge of the capacitor is interrupted and/or reduced. Decoupling the capacitor from the conductive path may also decouple the ablation target from receiving the waveform in some embodiments. Selective coupling and decoupling of a capacitor or other waveform source may be referred to as "chopping."

Figure 3:
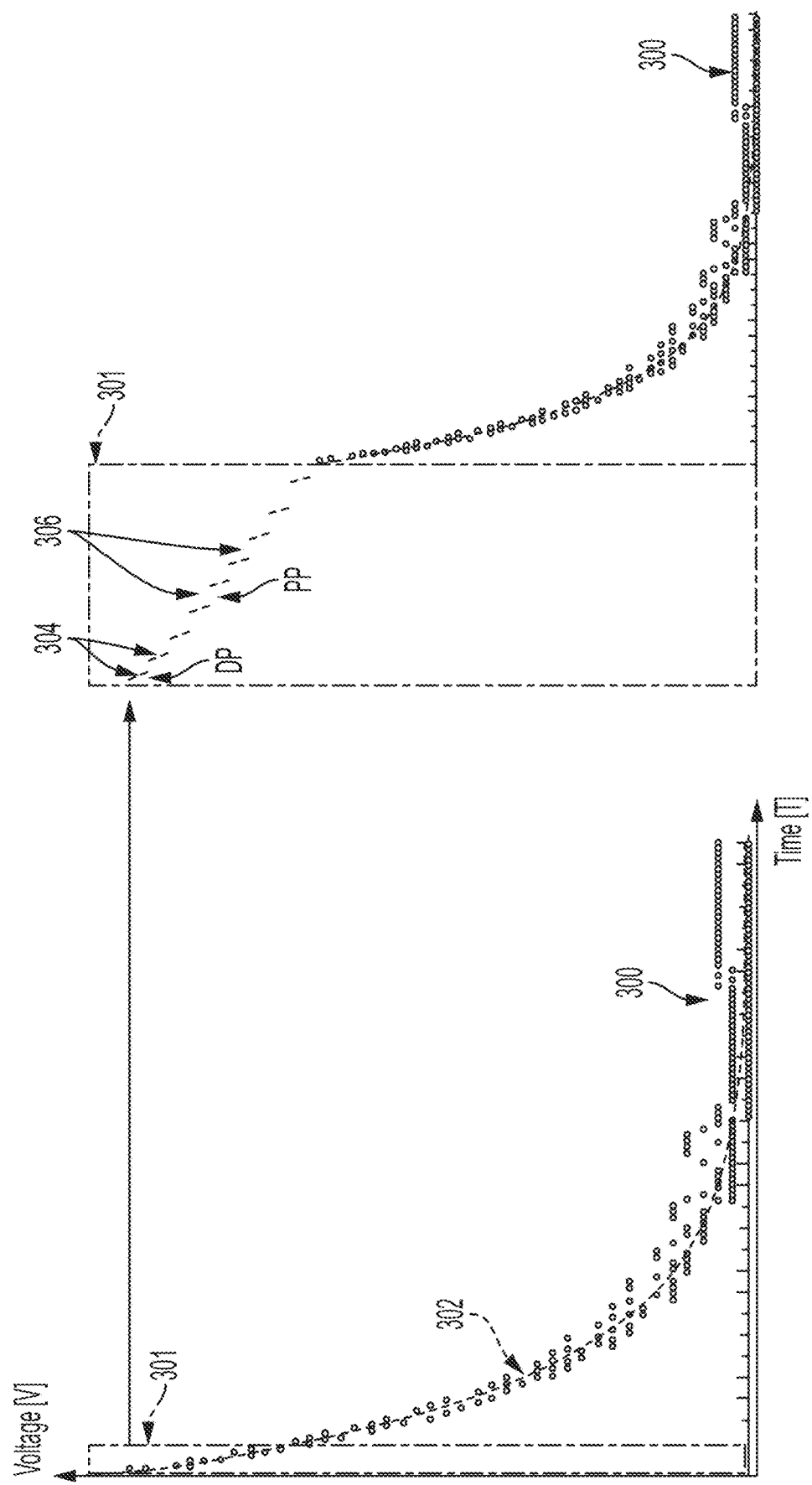
FIG. 3 is a plot of an example modulated waveform according to principles of the present disclosure.

FIG. 3 is a plot of an example modulated waveform 300 according to principles of the present disclosure. The modulated waveform 300 is plotted as a function of voltage over time. In this example an exponential decay as measured in liver tissue is shown in the plot on the left of FIG. 3. The solid line 302 is a line of best-fit for the modulated waveform 300 while the "dots" are the measured voltage values of the waveform 300. The green box 301 denotes a time interval of interest and is shown expanded on the right of FIG. 3. As illustrated, the decay in the time interval of interest in the green box 30 could be "stretched out." That is, the waveform 300 may be modulated to decrease the rate of decay during this period of the waveform. In this example, the modulated portion of the waveform 300 is when the waveform has a high voltage. However, in other examples, the time interval of interest could be located in another region of the waveform 300, for example, later in time when the waveform 300 has decayed to a lower voltage. Or, the waveform may include multiple time intervals of interest. In some embodiments, the modulated waveform 300 may be stretched out via chopping with defined delivery periods (DP) 304 and pause periods (PP) 306. During DP 304, the voltage of the waveform is delivered to the ablation target (e.g., liver tissue) and the waveform continues to decay. The DP 304 may also be referred to as "chops." During the PP 306, delivery of the voltage to the ablation target is interrupted and the decay of the waveform is halted and/or reduced.

In some embodiments, the waveform 300 may be modulated within a high voltage portion, which may contribute, at least in part, to electropermeabilization of tissue. In some embodiments, this may reduce the discharge probability if timed appropriately. In some embodiments, the waveform 300 may be modulated within a lower voltage portion. A longer low-voltage tail may contribute, at least in part, to the electrolysis in tissue. In some embodiments, rather than limited to a time interval of interest, the waveform 300 may be modulated across the entire waveform. In some applications, this may increase the ablation effect, lower the discharge probability, and/or increase ablation volume.

The initial voltage of waveform 300, the duration of DP, the duration of PP, the number of DP, the time interval of interest where the waveform is chopped may vary according to principles of the present disclosure. The parameters may be subject to the desired application in some cases. For example, parameters may be adjusted to improve electroporation efficiency, avoidance of arcing and/or plasma discharges and/or heating and/or reduction of muscle contractions during E2.

Arcing and/or plasma formation between electrodes, depending on the applied field strength, may take time to form. Accordingly, stopping and/or pausing delivery of the waveform to the ablation target by modulating the waveform by chopping may reduce or eliminate these effects in some embodiments. The stopping and/or pausing of delivery may be predetermined (e.g., programmed into a controller, such as controller 206) and/or on occurrence of arcing/plasma formation/plasma discharge as determined by a sensor (e.g., sensor 212) in communication with a controller in some embodiments. In these embodiments, continuous delivery of the waveform could be re-enabled once a detected voltage, field strength, resistance, and/or other parameter detected by the sensor has dropped below an arcing and/or plasma field threshold value. In some embodiments, ablation volumes in the ablation target may be increased in short treatment times by avoidance of plasma formations.

In some embodiments, stopping and/or pausing delivery of the waveform may provide control of the discharge intensity (e.g., pressure wave) which may provide control over a distance (e.g., radial distance) electrolytic products generated by the waveform are distributed through the ablation target with each discharge.

In some embodiments, chopping may allow for steep flanks in the modulated waveform delivered to the ablation target. This may provide for increased efficiency of the electroporation effect as some studies have shown that steep flanks may improve electroporation induction in some applications.

Reduction or elimination of muscle contractions may be achieved in some embodiments by choosing DP and/or PP durations that may minimally or gradually polarize the muscle endplate.

In addition to chopping, the voltage, current, or energy of the waveform may be modulated in some embodiments. For example, the voltage, energy, current, and/or charge of a specific part of the waveform to a desired level may be performed. For example, the voltage and/or current may be decreased to within safety margins for sensitive tissue and/or discharge control. In some embodiments, the waveform may be modulated to control the temperature increase on the electrode surface and/or ablation target in electrode vicinity to reduce or avoid thermal damage. For example, the voltage, current, and/or DP and/or PP durations may be adjusted by a controller based on a temperature detected by a sensor.

In some embodiments, the polarity of the waveform can be modulated. Changes in polarity include, but are not limited to reverse-polarity, bi-polar, or bi-phasic chops. In some embodiments, modulating the polarity may increase electroporation efficacy and reduce electrolysis and/or reduce plasma formation and/or discharges. In some applications, increased electroporation and reduced electrolysis may be desired. In some examples, modulation of polarity may be applied in a high voltage phase of the waveform to allow for longer and more electroporation-efficient phases before PP. Modulation of the polarity may be followed by mono-polar and/or nonpolar chopping at a lower voltage phase of the waveform.

In some embodiments, the consecutive application of several modulated waveforms with different properties may be used to maximize the ablation effect, lower the discharge probability or increase ablation volume.

Figure 4:
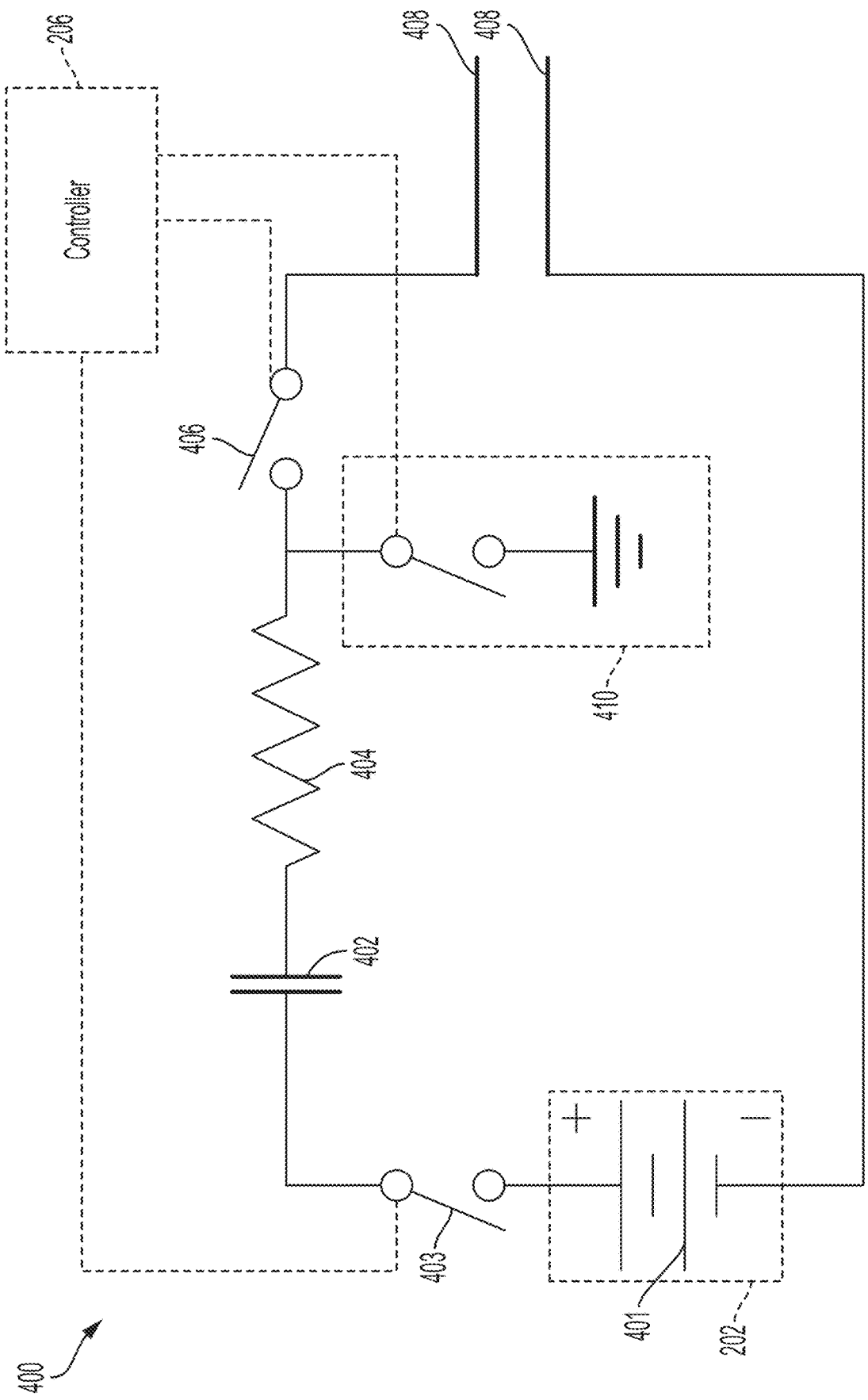
FIG. 4 is circuit diagram of an example apparatus for generating the modulated waveform according to principles of the present disclosure.

FIG. 4 is circuit diagram of an example apparatus 400 for generating the modulated waveform according to principles of the present disclosure. In some embodiments, the apparatus 400 may be used to implement at least a portion of the power supply 202, waveform generator 204, and/or controller 206. The apparatus 400 may be used for generating and modulating waveforms according to principles of the present disclosure, such as waveform 300 shown in FIG. 3. The apparatus 400 may include a capacitance 402, a resistance 404, and a switch 406.

The capacitance 402 may include a capacitor in some embodiments. The capacitance 402 may be charged to a desired level by coupling the capacitance 402 to a voltage source 401, for example, via a power supply, such as power supply 202. In some embodiments, the capacitance 402 may be selectively coupled to the voltage source 401 by a switch 403 controlled by a controller (e.g., controller 206). The capacitance 402 may be coupled to the resistance 404. The resistance 404 may include a resister in some embodiments. The capacitance 402 may be discharged through the resistance 404. The values of the capacitance 402 and resistance may be based, at least in part, on a charge and/or decay rate desired. In some embodiments, the capacitance 402 may include multiple capacitors which may allow for the maximum charge to be varied. In some embodiments, the resistance 404 may be a variable resistance which may allow for the decay rate to be varied.

The resistance 404 may be electrically coupled to one or more electrodes 408 and/or other conductive elements. A voltage and/or current provided by the capacitance 402 discharging through the resistance 404 may be provided to an ablation target via the one or more electrodes 408, which may be placed at, in, and/or the vicinity of the ablation target.

In some embodiments, the switch 406 may be coupled between the resistance 404 and the one or more electrodes 408. In other embodiments, the switch 406 may be coupled between the resistance 404 and the capacitance 402. The switch 406 may be controlled (e.g., by controller 206) to selectively couple the resistance 404 to the one or more electrodes 408. In some embodiments, the switch 406 may be a solid state switch. When the switch 406 is closed (e.g., on), the current and/or voltage from the capacitance 402 may be delivered to the ablation target. When the switch 406 is open (e.g., off), the current and/or voltage from the capacitance 402 is prevented from being delivered to the ablation target. In some embodiments, when the switch 406 is open, the capacitance 402 is decoupled from a conductive path for discharge. That is, the discharge of the capacitance 402 may be halted and/or reduced. Alternatively, in some embodiments, the switch 406 (or switch 406 in combination with another switch) may selectively couple the capacitance 402 to an alternative conductive path for discharge such that the capacitance 402 continues to discharge but the voltage and/or current is not delivered to the ablation target as illustrated by box 410.

In some embodiments, additional switches 412 and/or capacitances 402 (not shown) may be included such that a polarity of the voltage and/or current to the ablation target may be switched to modulate the waveform.

Figure 5:
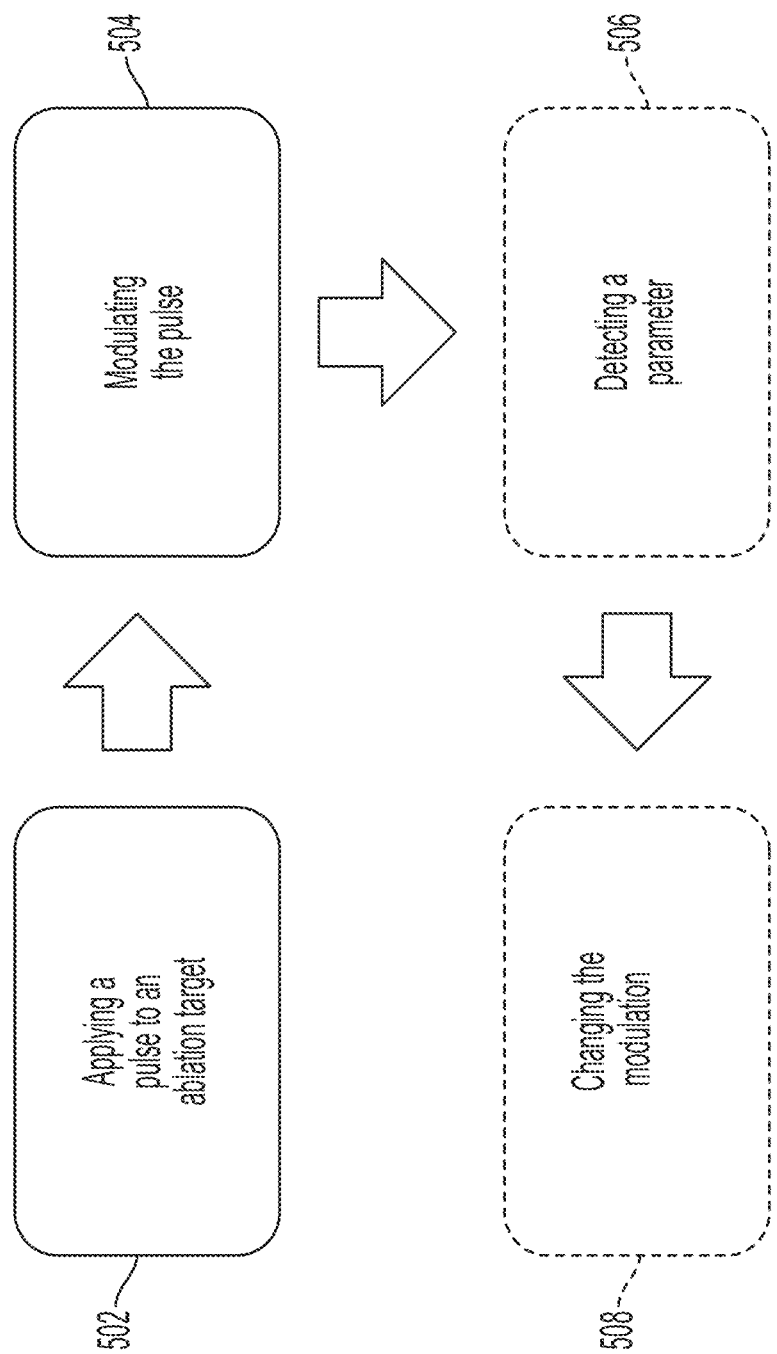
FIG. 5 is a flowchart of a method according to principles of the present disclosure.

FIG. 5 is a flowchart of a method 500 according to principles of the present disclosure. In some embodiments, some or all of the method 500 may be performed by the system 200 shown in FIG. 2 and/or apparatus 400 shown in FIG. 4. In some embodiments, the method 500 may be used to ablate tissue via E2.

An example technique for modulating waveforms includes interval delivery of the energy of a waveform for E2 to an ablation target (e.g., tissue) via one or more electrodes using solid state switches (e.g., switch 406) selectively coupling a capacitance (e.g., capacitance 402) to the one or more electrodes. A defined delivery period (DP) may be follow by a defined pause period (PP). The DP and/or PP may change over time. The DP and PP may be repeated multiple times, which may be referred to as a number of chops, in some embodiments. The initial voltage and/or current, DP, PP, number of chops, and/or changes in polarity of the waveform may be based on functions and/or real time voltage, current, impedance, light/optical and/or other feedback.

As shown in FIG. 5, at block 502, a step of "Applying a pulse to an ablation target" may be performed. The pulse may a voltage pulse, a current pulse, or a combination thereof in some embodiments. The pulse may have voltage and/or current values suitable for performing both electrolysis and electroporation (e.g., E2). The ablation target may be tissue, such as kidney or liver tissue in some embodiments. In some embodiments, the pulse may be generated by a waveform generator, such as waveform generator 204 and applied to the ablation target by one or more electrodes, such as electrodes 208. In some embodiments, the pulse may be generated, at least in part, by a capacitor, such as capacitance 402.

At block 504, a step of "Modulating the pulse" may be performed. Modulating the pulse may intermittently interrupt the application of the voltage and/or current to the ablation target in some embodiments. In some embodiments, modulating the pulse comprises selectively opening and closing a switch, such as switch 406. In some embodiments, the opening and closing of the switch may be controlled by a controller, such as controller 206. In some embodiments, the pulse may include a decay component and modulating the pulse may alter the decay component of the pulse. For example, it may increase or decrease a rate of decay of the pulse. In some embodiments, modulating the pulse may occur within a time interval of interest of the pulse. The time interval of interest may include only a portion of the pulse that is less than the entire pulse. In other embodiments, modulating the pulse may occur across the entire pulse.

In some embodiments, modulating the pulse may be based, at least in part, on a delivery period and a pause period. The voltage and/or current is applied during the delivery period and interrupted during the pause period. Modulating the pulse may further be based, at least in part, on a total number of delivery periods (e.g., chops) in some embodiments. The delivery period, pause period, and/or number of delivery periods may be preprogrammed (e.g., in the controller or a computing device coupled to the controller) or they may be dynamically altered as discussed further below.

Optionally, at block 506, a step of "Detecting a parameter" may be performed. The detection may be performed by a sensor, such as sensor 212, in some embodiments. The parameter may be detected in a vicinity of the ablation target in some embodiments. The parameter may be provided to the controller that controls the modulation of the pulse. Parameters may include, but are not limited to, a voltage, an electric field, an impedance, light/optical and/or a temperature. In some embodiments, the sensor may be an imaging device such as an ultrasound or MRI machine. The imaging device may be able to detect an ablation volume or other parameter. When block 506 is performed, the modulating the pulse performed in block 504 may be based, at least in part, on a value of the parameter detected by the sensor. Thus, in some embodiments, blocks 504 and 506 may be performed simultaneously. In some embodiments, block 506 may be performed before block 504.

Optionally, at block 508, a step of "Changing the modulation" may be performed. For example, changing the modulation of the pulse may switch a polarity of the voltage and/or the current and/or change the DP and PP of the modulation and/or any other parameter of the modulation. In some embodiments, blocks 504 and 508 may be performed simultaneously. In some embodiments, block 508 may be performed before block 504. In embodiments where block 506 is also performed, blocks 508 and 506 may be performed simultaneously or block 508 may be performed before or after block 506. In some embodiments, blocks 504, 506, and 508 may be performed simultaneously.

Thus, the systems, apparatuses, and methods described herein may provide for modulating a pulse (e.g., waveform) for delivering E2 treatment to an ablation target, such as tissue. Modulating the pulse according to principles of the present disclosure may reduce the risk of arcing and/or discharge, increase ablation volume, and/or allow control over the individual effects of electroporation and electrolysis to the ablation process in some embodiments.

In some embodiments, DP, PP and number of chops may be defined statically. That is, they may be predefined, for example, by programming a controller (e.g., controller 206). In some embodiments, DP and PP may be predefined but instead of defining the number of chops a period of the chopping may be defined by tissue impedance and/or conductivity measurements, absolute voltage and/or current goal, analytics of the voltage and/or current or other parameters (e.g., slope of voltage decay). The parameters may be detected by one or more sensors (e.g., sensor 212) and provided to the controller. In some embodiments, DP and/or PP are dynamically adapted from real time acquired parameters (e.g., voltage, current, impedance, light/optical, temperature, Ultrasound, Magnetic Resonance Imaging) acquired by the one or more sensors. In these embodiments, the number of chops may also be dynamically determined from the parameters or predefined. In some embodiments, additional pauses or train-groups of DP/PP may be added either statically (e.g., pre-defined) or dynamically from real time values of parameters acquired by the one or more sensors.

In some embodiments, DP and PP may be defined but there is no defined number of chops. Instead the entire waveform is chopped. That is, there is no time interval of interest, or the entire waveform is within the time interval of interest. In some embodiments, DP and PP are dynamically adapted to reach a desired mean slope of the decay of the voltage and/or current. In some embodiments, DP may be programmed to increase in duration (e.g., from low microseconds to hundreds of microseconds) over a defined period of time to gradually stimulate muscle contractions.

In some embodiments, biphasic switching (polarity reversal) can be employed for additional electroporation effect and/or ion direction reversal/stopping or ionization reversal or reducing electrolysis production (for example in a high voltage phase of a waveform). In some applications, reducing electrolysis production during a high voltage phase may reduce arcing and/or discharge and/or influence the discharge plasma. In some embodiments, a lower voltage phase of a waveform may be extended by chopping to increase electrolysis. In some applications, this may increase the production and/or transport of electrolysis products at voltages where there is a lower risk of arcing and/or discharge.

In some embodiments the combination electrolysis and permeabilization may be combined with other modalities for tissue treatment such as thermal ablation, radiation, chemical ablation, and/or gene therapy.

Some specific experimental examples are provided below to facilitate appreciation of embodiments described herein. The experimental examples presented are not intended to be comprehensive or exhaustive of all experiments performed or of all results obtained. Examples I and II are directed to examples of a single exponential decay pulse without modulation. Examples III-V are directed to examples of pulses (e.g., waveforms) with modulation according to principles of the present disclosure. Examples I and II are provided to help illustrate potential differences and/or advantages in results that may be achieved in some embodiments by modulating the exponential decay pulse or other waveforms according to principles of the present disclosure. Examples VI and VII are directed to example circuitry that may be used to implement at least a portion of system 200 in some embodiments. The circuitry in Examples VI and VII may be used to provide the pulses in Examples III-V in some embodiments.

Example I

Figure 6:
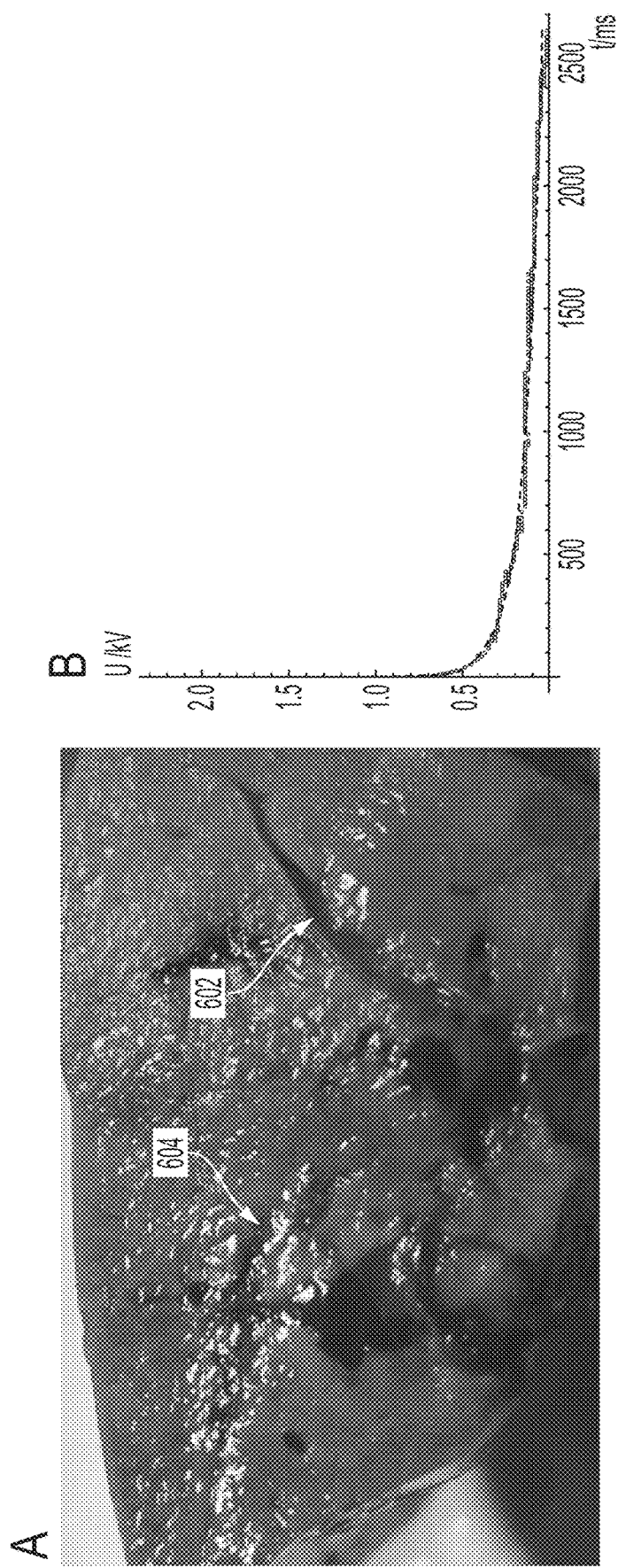
FIG. 6 illustrates the potentially detrimental effects of the initial high voltage and resulting uncontrolled discharge/plasma formation.

A first experimental study was carried out in vivo on three female pigs between 90 and 110 kg. The animals were fasted for 24 h and pre-medicated with a combination of diazepam (0.4 mg/kg) and ketamine (15 mg/kg). Anesthesia was induced with intravenous (IV) Propofol (3 mg/kg). Endotracheal intubation was performed and anesthesia was maintained with sevoflurane in oxygen (adjusted to 1.8-2% End tidal sevoflurane). Possible postoperative pain was treated with Buprenorphine 0.01 mg/kg IM Pre-med at recovery and Carprofen 4 mg/kg at extubation/recovery. Cefazolin 25 mg/kg IV was administrated every 2 h. If found to be needed during the procedure, the study had the ability to deliver pancuronium (0.1 mg/kg, at a dose of 1 mg/ml) through an IV to reduce muscle contractions during the application of the electrical waveforms. The liver was exposed via a midline incision. The treatment was delivered using a custom made apparatus with two 18-gauge Titanium electrodes (Inter Science GmbH, Ch) at variable exposed length at 1 cm distance. Further relevant parameters of the treatment were: e=1 cm, C=100 µF, U=2250V. As shown in panel A of FIG. 6, gross pathology of the treatment site revealed the effects of violent discharge through burst vessels 602 and heavy hemorrhage 604. As shown in panel B of FIG. 6, the oscilloscope trace showed that the applied exponential decay voltage experienced a significant voltage drop from 2000V to approx. 500V within the first 100 ms, resulting in this violent discharge.

Example II

Figure 7:
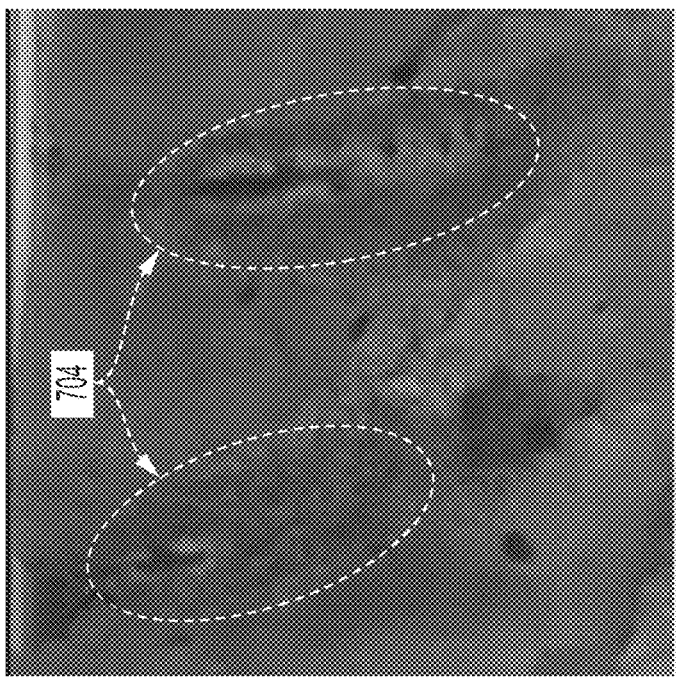
FIG. 7 illustrates the avoidance of the effects shown in FIG. 6 through application of lower initial voltage.
Figure 7:
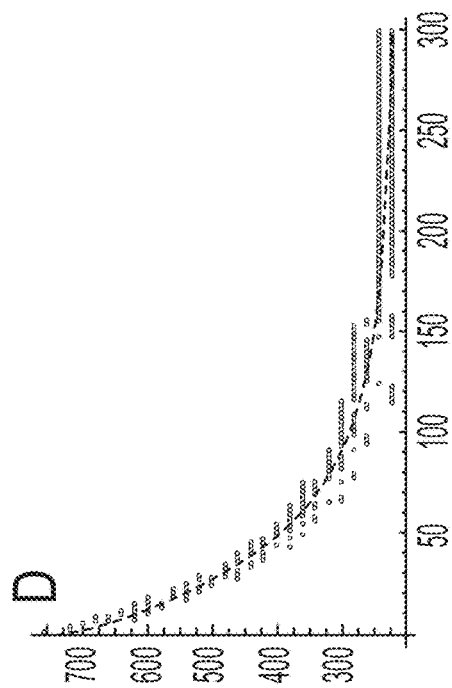
Figure 7:
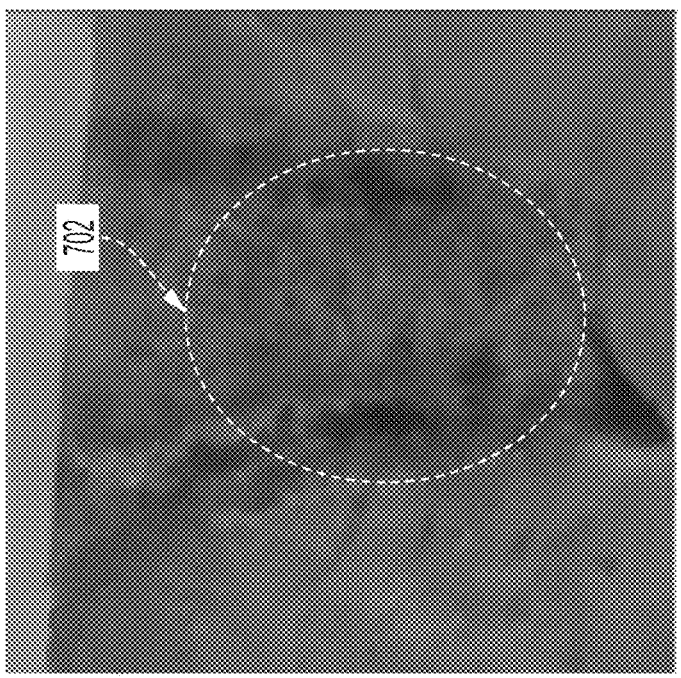
Figure 7:
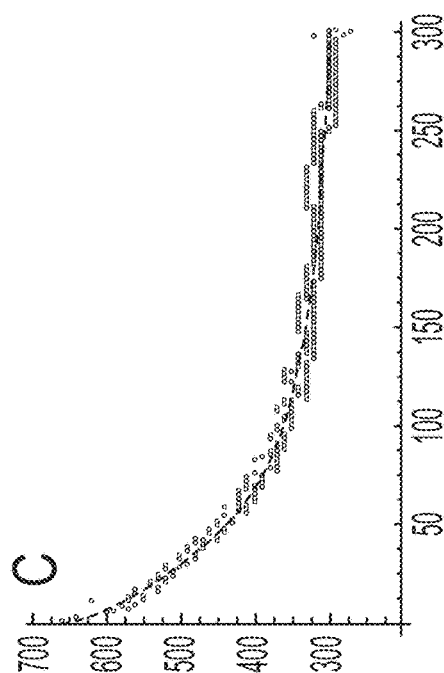

A second experimental study was carried out in vivo on a 80 kg female pig. After being fasted for 24 hours, the animal was pre-medicated with a combination of acepromazine (0.5 mg/kg) and ketamine (15 mg/kg) injected intramuscularly (IM). Anesthesia was induced with intravenous (IV) Propofol (2.5 mg/kg) and 0.1 mg Fentanyl. Endotracheal intubation was performed and anesthesia was maintained with sevoflurane in 80% oxygen (adjusted to 2-2.5% End-tidal sevoflurane). Possible postoperative pain was treated with morphine 0.1 mg/kg IM and ketoprofen 1 mg/kg q 6 hours. Cefazolin 25 mg/kg IV was administrated every 2 hours. The pig was placed in a ventral side-up position, and restrained using strings. The liver was exposed via an upper midline incision continued with a right transverse incision. The treatment was delivered using two 18-gauge Titanium needles (Inter Science GmbH, Switzerland) with a variable length (1-4 cm) insulating sheath inserted in the liver, placed under ultrasound-guidance (Hi Vision Preirus Ultrasound device, Hitachi Medical Systems, Germany). An E2 application was performed using a custom apparatus with parameters: e=1.5 cm, C=122 µF, U1=500V and U2=1100V at 1 cm distance between electrodes. The gross pathology is shown in panel A of FIG. 7 and the waveform is shown in panel C of FIG. 7. An E2 application was also performed using a custom apparatus with parameters: e=1.5 cm, C=122 µF, U1=500V and U2=1100V at 1.5 cm distance between electrodes. The gross pathology is shown in panel B of FIG. 7 and the waveform is shown in panel D of FIG. 7.

The entire treatment region 702 is lethally affected in panel A as per histological examination. With increasing distance between electrodes, however, the treatment area is only partially affected as shown by circles 704 in panel B, even though more charge/electrolysis was applied. This demonstrates that while lower voltage may be one way to solve the problem of uncontrolled discharge, it may have limits in its application regarding lesion dimensions.

Example III

According to a first non-limiting example of the present disclosure, a plastic container was used to cast an agar gel phantom made of physiological saline (1 g/L Agar, 0.9% w/V NaCl) to quantify plasma formations by analyzing physical damage of the gel and brilliance of the discharge.

Sucrose was added in the amounts needed to simulate the conductivity of liver and kidney tissue, respectively.

For the experiments, one pair of stainless steel electrodes of 1.8 mm diameter was inserted into the phantom, at distances and with exposure lengths as described for each experiment, and electrolytic electroporation (E2) was applied with a custom-made apparatus, with parameters as described in reference to FIGS. 8-13. A single E2 waveform was applied. The custom-made apparatus included a charge/discharge circuit with arbitrary selectable capacity from several ports in the kilovolt range, and an IGBT H-Bridge based discharge control circuit to modify the waveform in <=1 microsecond precision for the output ports leading to the tissue. An additional bypath resistor allowed further discharge waveform modulation. For the large animal studies, the output ports were stacked to allow the use of electrode arrays.

Studies have revealed that brilliance correlates with significance of discharge. To acquire brilliance during treatment, a digital camera (Panasonic Lumix DMC-G81MEG-K) with manual long time exposure settings (Iso100, F3.5, 12 mm, 10" exposure time, color mode normal, white balance 5000 k) was used in an otherwise black box to acquire images of arcing and/or discharges (if present). The applied voltage was detected with an oscilloscope (Owon Sds7102V with a differential probe Pico TA044).

Figure 8:
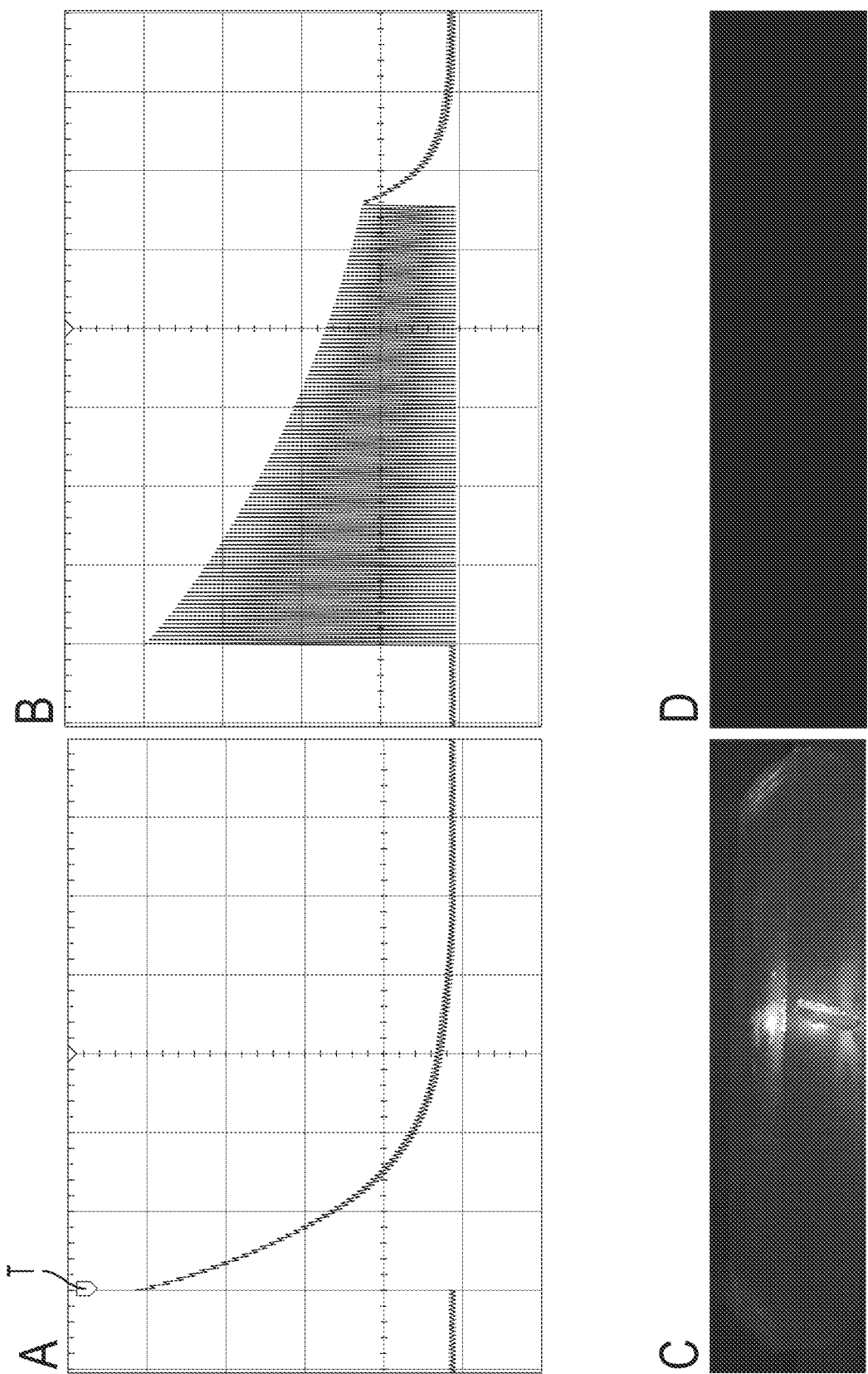
FIG. 8 illustrates the effect of a single modulated waveform as mono-polar chopped waveform applied in liver tissue phantom according to principles of the present disclosure.

FIG. 8 illustrates a comparison between a high voltage continuous exponential decay pulse and a high voltage mono-polar waveform modulated by chopping according to principles of the present disclosure. Experiments were obtained in liver agar phantom, with parameters C=293 μF, U=2000V, d=2 cm, e=3 cm; needle electrodes with 1.8 mm thickness were applied. Panel A illustrates the continuous exponential decay without chopping measured in the phantom. Panel C is an image of a discharge due to arcing and/or plasma discharge in the phantom. Panel B illustrates the modulated waveform including 1000 chops (DP) of 100 μs length, 1 ms pauses (PP) in between them measured in the phantom. Panel D is an image showing that no arcing or discharging occurred in the phantom.

Figure 9:
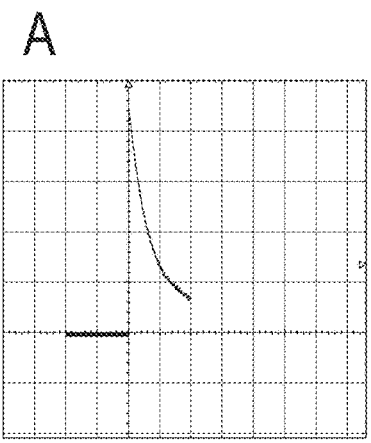
FIG. 9 illustrates the effect of a single modulated waveform as mono-polar chopped waveform applied in liver tissue phantom according to principles of the present disclosure.
Figure 9:
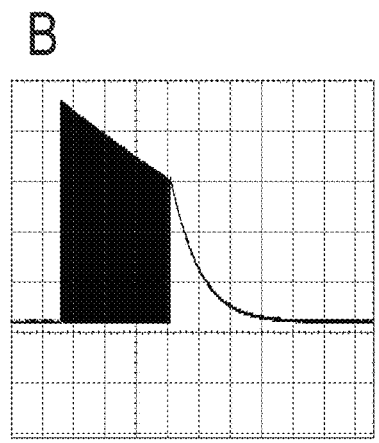
Figure 9:
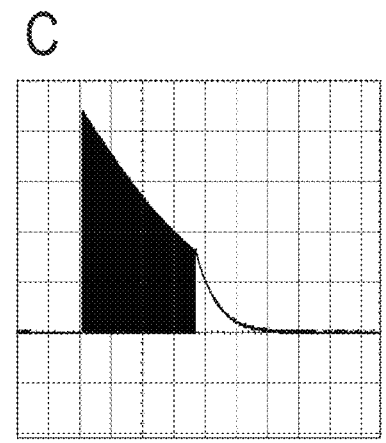
Figure 9:
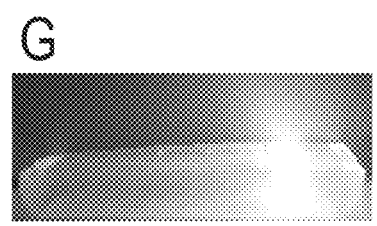
Figure 9:
Figure 9:
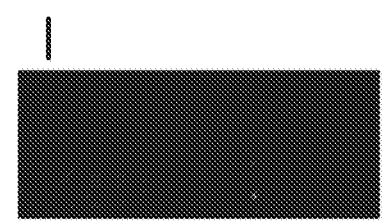
Figure 9:
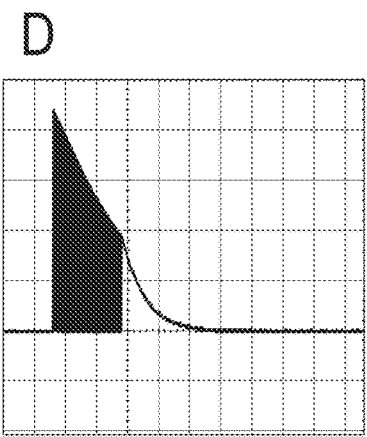
Figure 9:
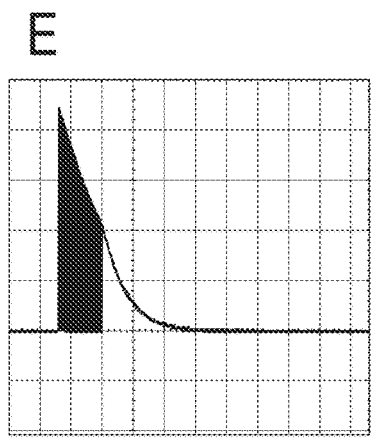
Figure 9:
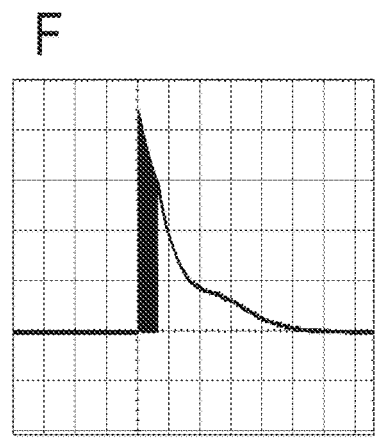
Figure 9:
Figure 9:
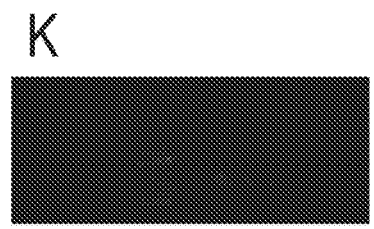
Figure 9:
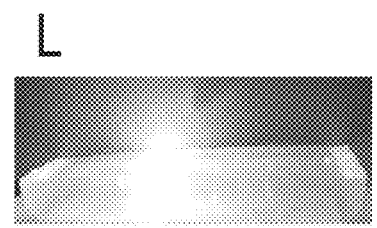

FIG. 9 illustrates comparisons between a continuous exponential decay at high voltages compared to modulated waveforms with mono-polar chopping at the high voltage phase with different timings and counts according to principles of the present disclosure. Experiments were obtained in liver agar phantom. Application of single waveforms with parameters: U=2300V, d=2 cm, e=3 cm, C=300 μF, needle electrodes with 1.8 mm thickness.

Panel A shows a continuous exponential decay waveform as measured in the phantom. Panel G is an image of a discharge due to arcing and/or plasma discharge in the phantom. Panel B shows a modulated waveform having 3000 DPs of 10 μs length, 100 μs PP between DP. Panel C shows a modulated waveform having 3000 DPs of 20 μs length, 100 μs PP between DP. Panel D shows a modulated waveform having 1500 DPs of 40 μs length, 100 μs PP between DP. Panel E shows a modulated waveform having 750 DPs of 80 μs length, 100 μs PP between CHOPs. Panel F shows a modulated waveform having 300 DPs of 100 μs length, 100 μs PP between DPs. The scale for all waveforms is one square equals 500V/100 ms. Panels H-K are images showing that no arcing or discharging occurred in the agar phantom for the waveforms in panels B-E, respectively. Panel L is an image of a discharge due to arcing and/or plasma discharge in the phantom associated with the waveform delivered in panel F.

Figure 10:
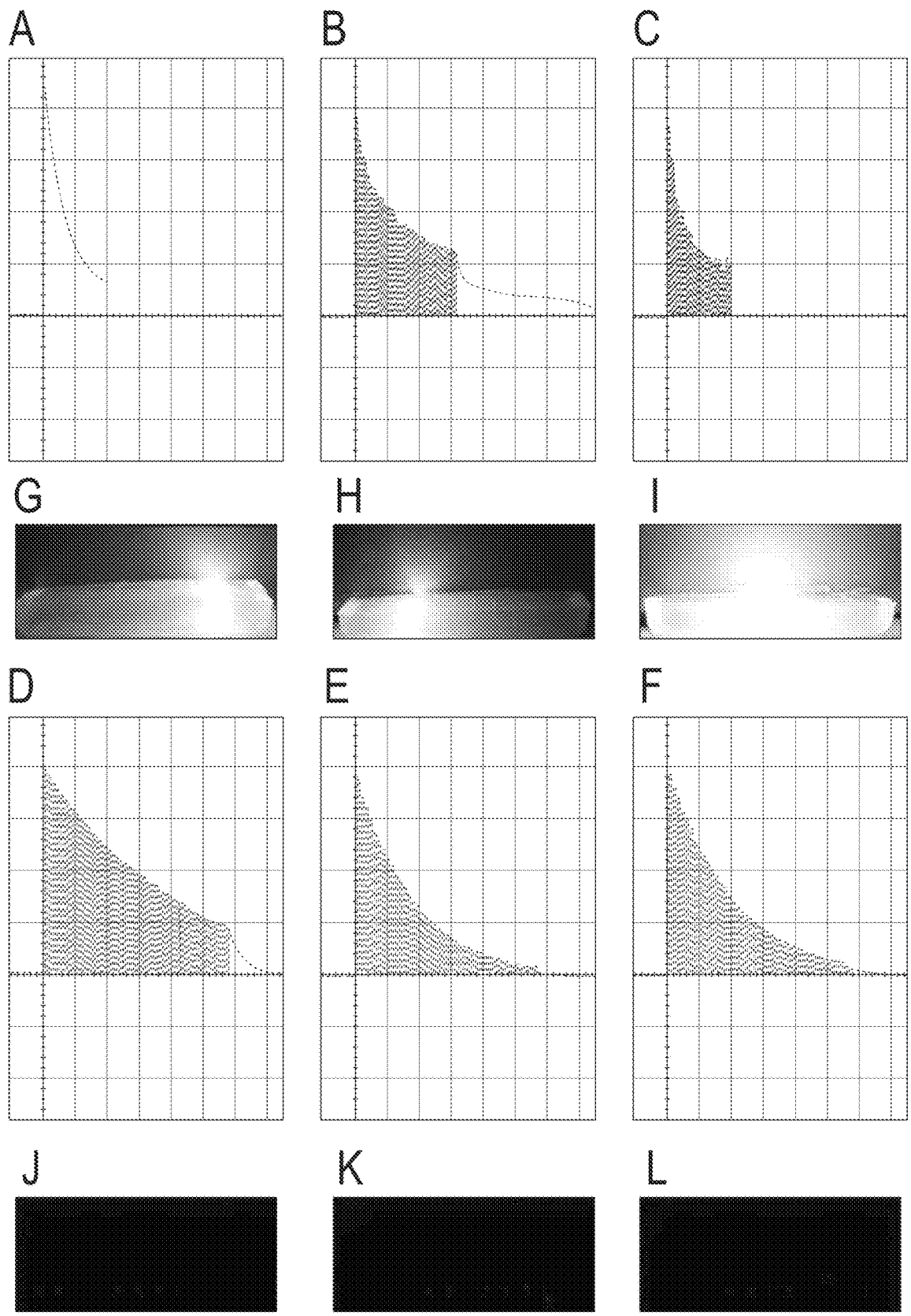
FIG. 10 illustrates the effect of a single modulated waveform as mono-polar chopped waveform applied in kidney tissue phantom according to principles of the present disclosure.

FIG. 10 illustrates a continuous exponential decay at high voltages compared to modulated waveforms with mono-polar chopping at the high voltage phase with different timings and counts according to principles of the present disclosure. Experiments were obtained in kidney agar phantom. Application of single waveforms with parameters: U=2300V, d=2 cm, e=3 cm, C=300 μF, needle electrodes with 1.8 mm thickness.

Panel A shows a continuous exponential decay waveform as measured in the phantom. Panel G is an image of a discharge due to arcing and/or plasma discharge in the phantom. Panel B shows a modulated waveform having 1250 DPs of 20 μs length, 100 μs PP between DP. Panel C shows a modulated waveform having 1250 DPs of 80 μs length, 100 μs PP between DP. Panel D shows a modulated waveform having 1250 DPs of 10 μs length, 100 μs PP between DP. Panel E shows a modulated waveform having 1250 DPs of 20 μs length, 200 μs PP between DP. Panel F shows a modulated waveform having 1250 DPs of 40 μs length, 400 μs PP between DP. The scale for all waveforms is one square equals 500V/100 ms. Panels H and I are images of discharges due to arcing and/or plasma discharge in the phantom associated with the waveforms delivered in panels B and C, respectively. Panels J-L are images showing that no arcing or discharging occurred in the agar phantom for the waveforms in panels D-E, respectively.

Figure 11:
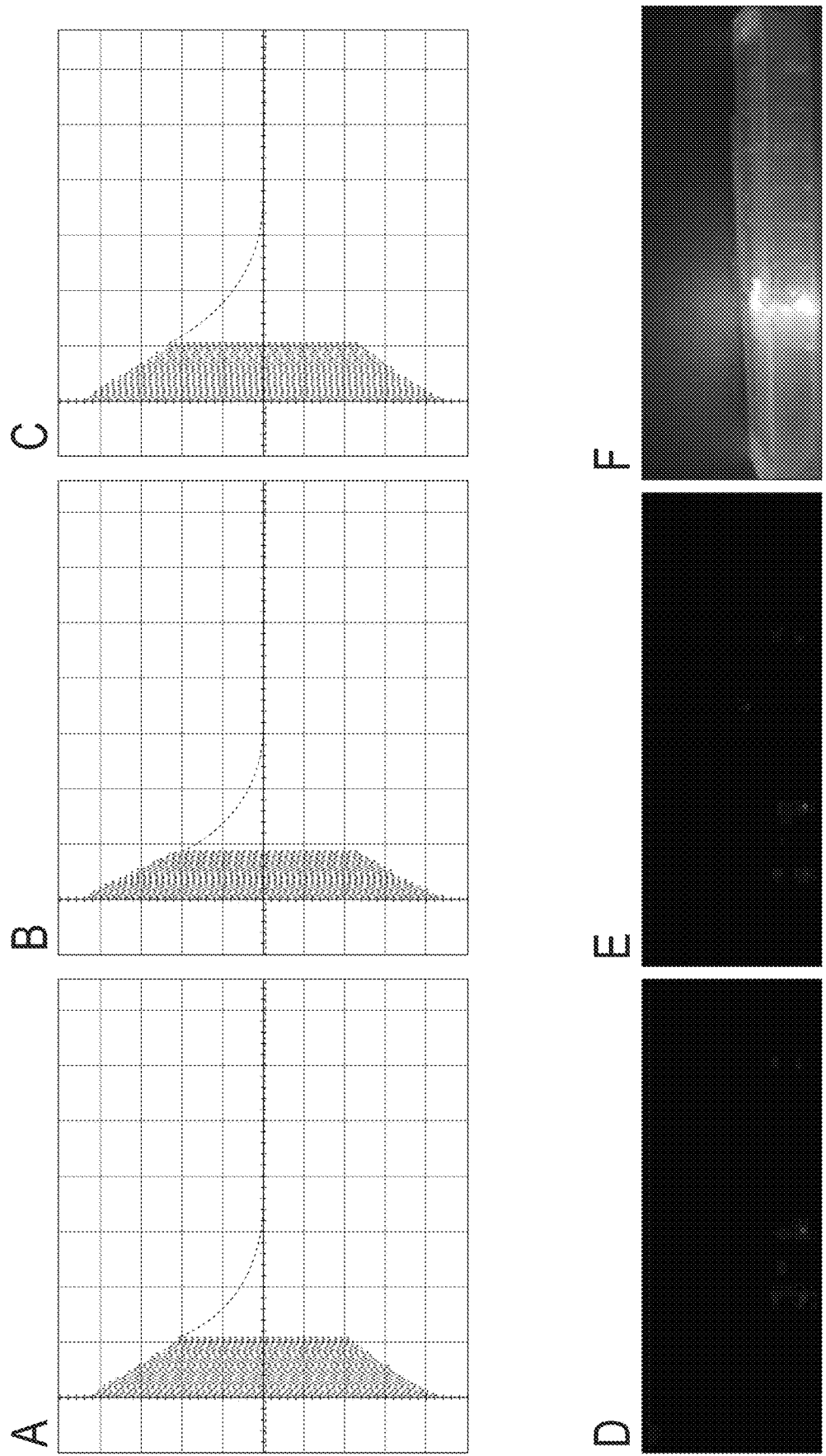
FIG. 11 illustrates the effect of a single modulated waveforms as bi-polar chopped waveform applied in liver tissue phantom according to principles of the present disclosure.

FIG. 11 illustrates modulated bi-polar waveforms with chopping at a high voltage phase according to embodiments of the present disclosure. Bi-polar waveforms may reduce or eliminate strong discharges or plasma formations at high voltages in some applications. Experiments were obtained in liver agar phantom. Application of single waveforms with parameters: U=2300V, d=2 cm, e=3 cm, C=300 μF, needle electrodes with 1.8 mm thickness. Panel A shows a modulated waveform having a time of high plateau DP 10 μs, PP 10 μs, time of low plateau DP 10 μs, PP 10 μs. Panel B shows a modulated waveform having a time of high plateau DP 10 μs, PP 2 μs, time of low plateau DP 10 μs, PP 2 μs. Panel C shows a modulated waveform having a time of high plateau DP 10 μs, PP 2 μs, time of low plateau DP 2 μs, PP 2 μs. The scale for all wave forms is one square equals 500V/100 ms. Panels D-E are images showing that no arcing or discharging occurred in the agar phantom for the waveforms in panels A-B, respectively. Panel F is an image of discharge due to arcing and/or plasma discharge in the phantom associated with the waveform delivered in panel C.

Figure 12:
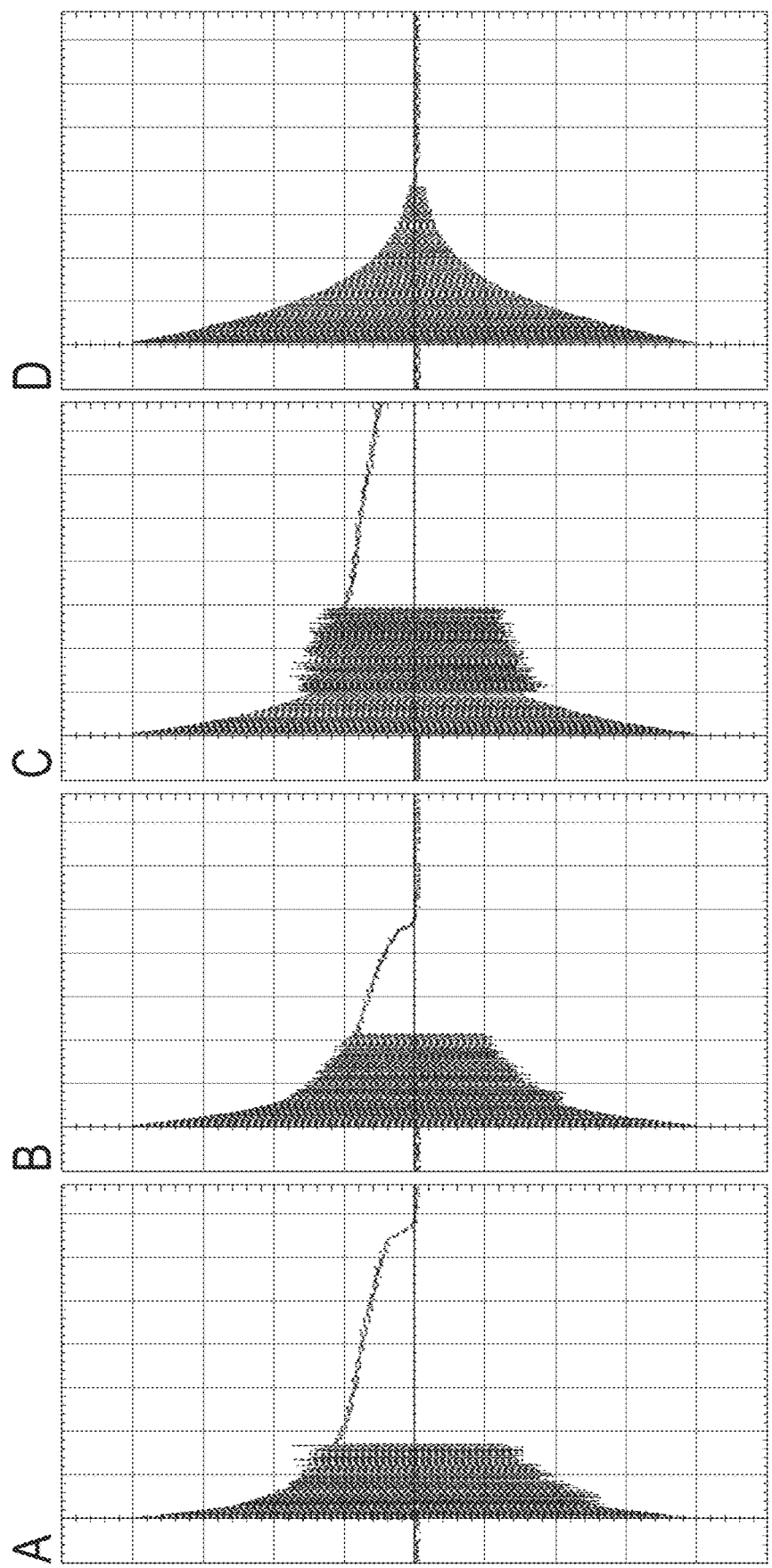
FIG. 12 illustrates the effect of a single modulated waveforms as bi-polar chopped waveform applied in kidney tissue phantom according to principles of the present disclosure.
Figure 12:
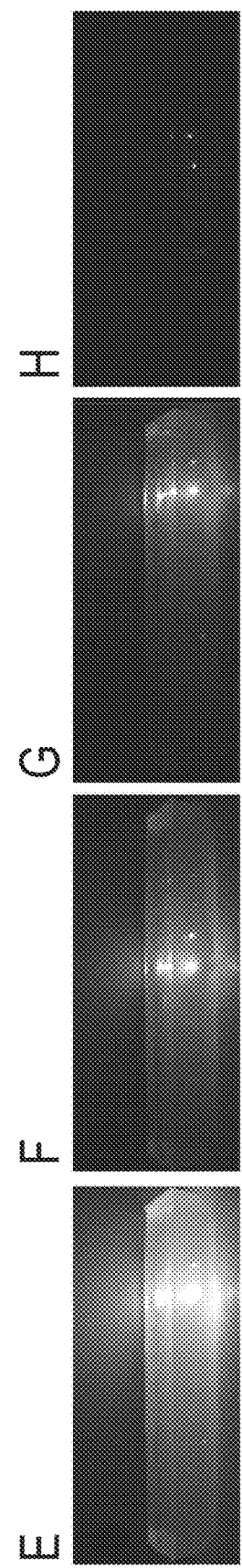

FIG. 12: illustrates modulated bi-polar waveforms with chopping at a high voltage phase according to embodiments of the present disclosure. Experiments were obtained in kidney agar phantom. Application of single waveforms with parameters: U=2300V, d=2 cm, e=3 cm, C=300 μF, needle electrodes with 1.8 mm thickness. Panel A shows a modulated waveform having a time of high plateau 40 μs, pause time 150 μs, time of low plateau 10 μs, low plateau 3× in a row. Panel B shows a modulated waveform having a time of high plateau DP 60 μs, PP 200 μs, time of low plateau DP 10 μs, with a low plateau DP 3× in a row. Panel C shows a modulated waveform having a time of high plateau DP 60 μs, PP 300 μs, time of low plateau DP 10 μs, with a low plateau DP 3× in a row. Panel D shows a modulated waveform having a time of high plateau DP 60 μs, PP 400 μs, time of low plateau DP 5 μs, with a low plateau DP 3× in a row. The scale for all waveforms is one square equals 500V/200 ms. Panels E-G are images of discharge due to arcing and/or plasma discharge in the phantom associated with the waveforms delivered in panels A-C, respectively.

Panel H is an image showing that no arcing or discharging occurred in the agar phantom for the waveform in panel D.

Figure 13:
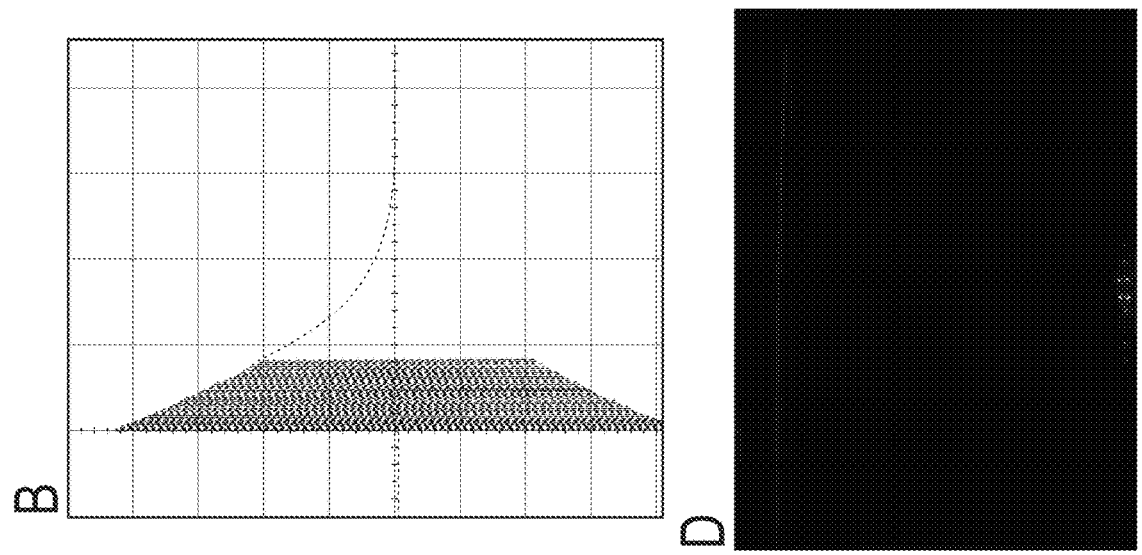
FIG. 13 illustrates the direct comparison of a single modulated waveform as mono-polar and bi-polar chopped waveform according to principles of the present disclosure.
Figure 13:
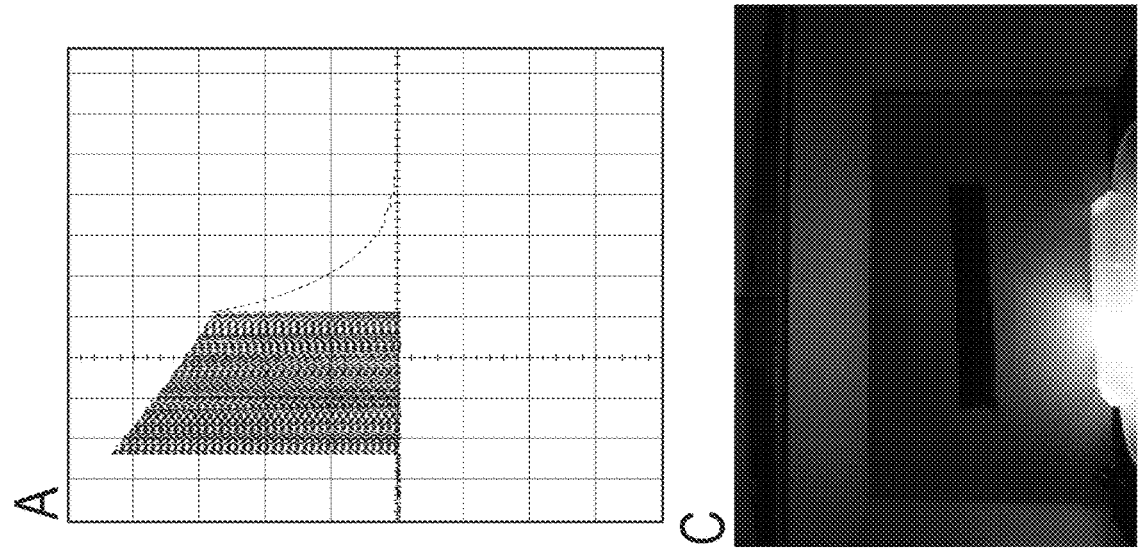

FIG. 13 illustrates a comparison between a mono-polar modulated waveform according to principles of the present disclosure and a bi-polar modulated waveform according to principles of the present disclosure. Panel A shows a mono-polar modulated waveform having 80 μs DPs with 100 μs PPs. Panel B shows a bi-polar modulated waveform having a 80 μs positive DP, 2 μs PP, 8 μs negative DP, 2 μs PP. The applications in A and B employed the same voltage and the same capacitance in the same gel phantom. Panel C is an image of discharge due to arcing and/or plasma discharge in the phantom associated with the waveform delivered in panel A. Panel D is an image showing that no arcing or discharging occurred in the agar phantom for the waveform in panel B. This experiment demonstrates that bi-polar chopping may result in less discharge than mono-polar chopping of waveforms having the same amount of energy, even when the energy delivery speed in the bipolar example is higher.

All experiments in Example III demonstrate that modulated waveforms may be a useful tool to implement in the high voltage phase to reduce or prevent violent discharge and/or plasma formations. Modulating waveforms according to principles of the present disclosure may safely allow for higher initial voltages during E2, which may potentially allow for larger ablation volumes and/or faster application of E2.

Example IV

According to a second non-limiting example of the present disclosure, a plastic container was used to cast an agar gel phantom made of physiological saline (1 g/L Agar, 0.9% w/V NaCl) to quantify plasma formations by analyzing physical damage of the gel and brilliance of the discharge. Sucrose was added in the amounts needed to simulate the conductivity of liver and kidney tissue, respectively. For the experiments, one pair of stainless steel electrodes of 1 mm diameter was inserted into the phantom, at distances and with exposure lengths as described in reference to FIGS. 14A-B, and electrolytic electroporation was applied with the same apparatus as described in Example III, with parameters as described in reference to the respective figures. Three consecutive E2 waveforms were applied. Studies have revealed that brilliance correlates with significance of discharge. To acquire brilliance during treatment, the same equipment as described in Example III was used.

Figure 14A:
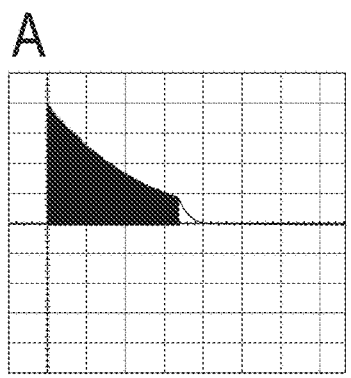
FIG. 14A-14B illustrates the effect of three consecutive modulated waveforms as mono-polar chopped waveforms applied in kidney tissue phantom according to principles of the present disclosure.
Figure 14A:
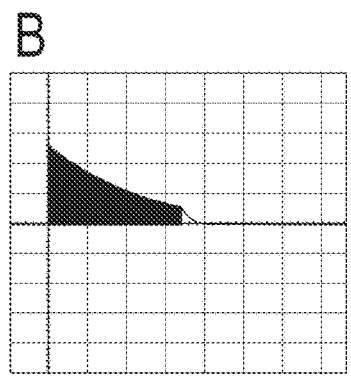
Figure 14A:
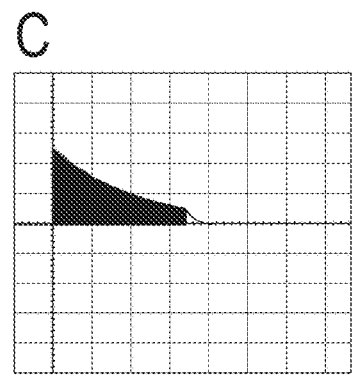
Figure 14A:
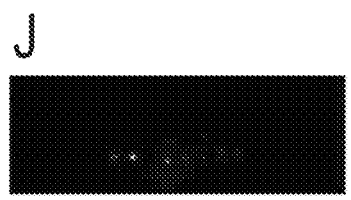
Figure 14A:
Figure 14A:
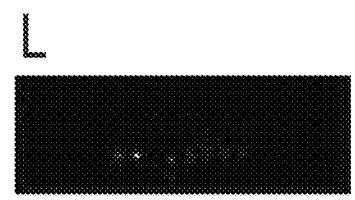
Figure 14A:
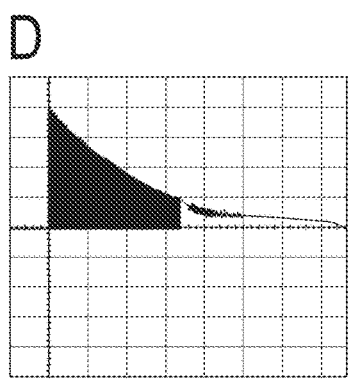
Figure 14A:
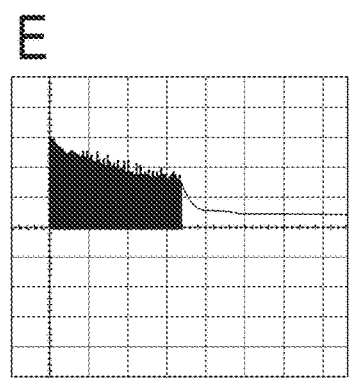
Figure 14A:
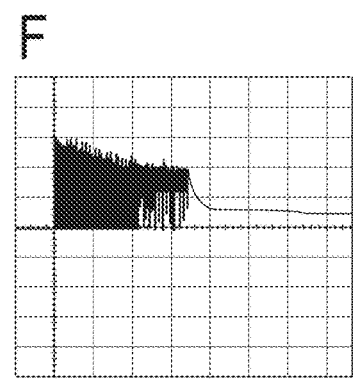
Figure 14A:
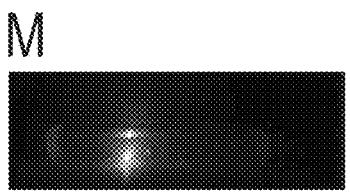
Figure 14A:
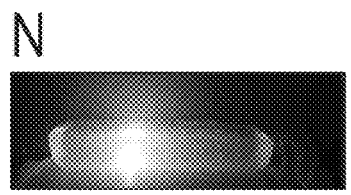
Figure 14A:
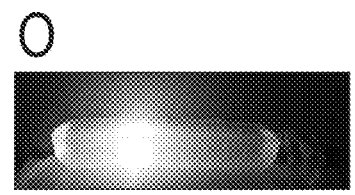

FIG. 14A illustrates the application of three consecutive waveforms modulated according to principles of the present disclosure. All of the waveforms were modulated with mono-polar chopping with 30 s between waveforms in a kidney phantom. Parameters include d=2 cm, e=3 cm, C=300 μF, and stainless steel needle electrodes with 1.8 mm thickness. The modulated waveforms included 40 μs DP, 400 μs PP, 750 total DPs. Panels A-C show waveforms having initial voltages of 2300V, 1500V, 1500V, respectively. Panels D-F show waveforms having initial voltages of 2300V, 1800V, 1800V, respectively. The scale for all waveforms is 1 square equals 500V/100 ms. Panels J-L are images showing that no arcing or discharging occurred in the phantom for the waveforms in panels A-C, respectively. Panels M-O are images of discharge due to arcing and/or plasma discharge in the phantom associated with the waveforms delivered in panels D-E, respectively. From this experiment, mono-polar chopping with parameters of 40 μs DP, 400 μs PP, and 750 total DPs, the maximum voltage of waveforms in panels B and C may be 1500V or arcing/discharge may occur. To reach higher voltages, it may be required to shorten the DP lengths and/or lengthen pause times, as shown in FIG. 7B.

Figure 14B:
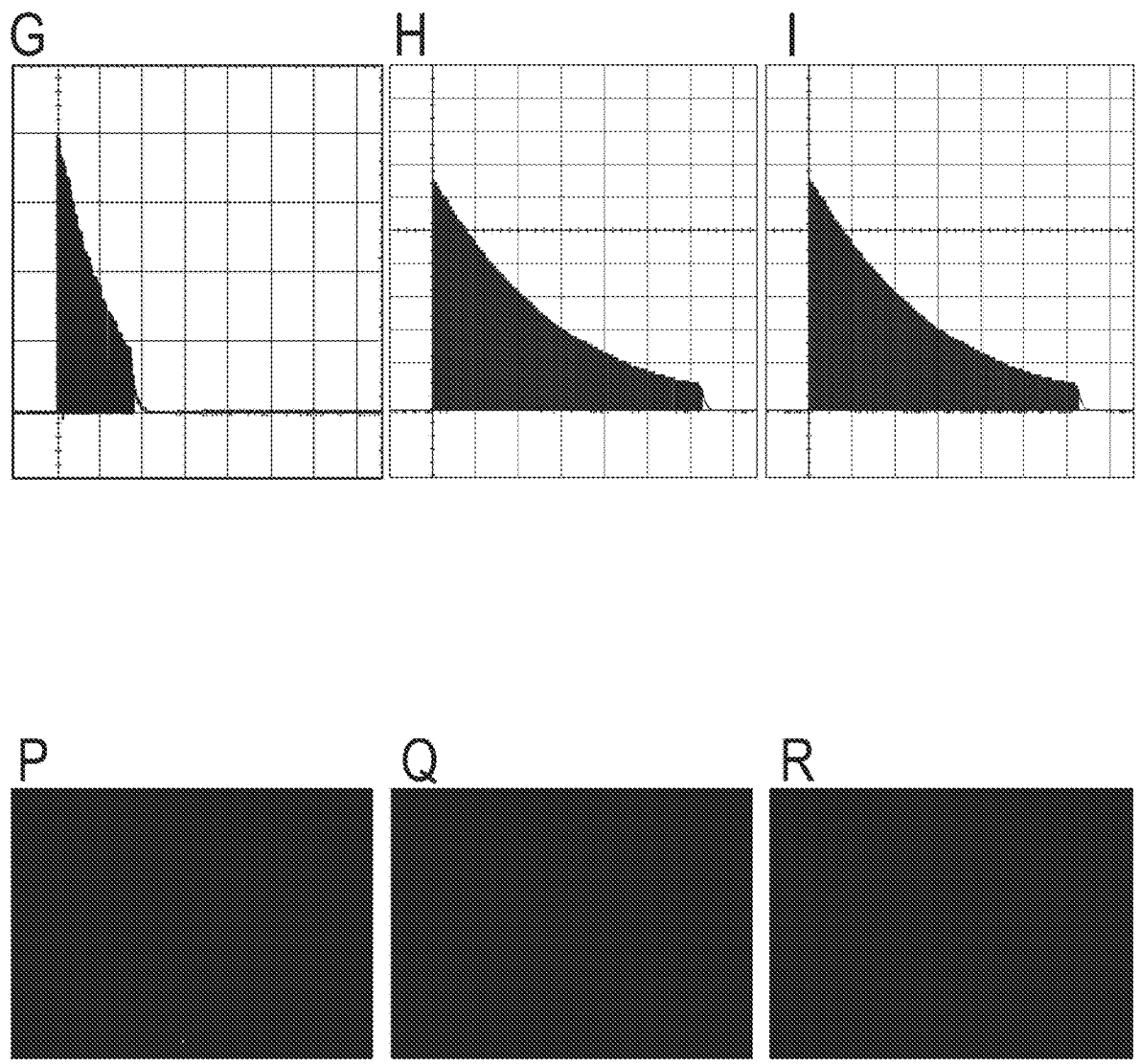

FIG. 14B illustrates the application of three consecutive waveforms modulated according to principles of the present disclosure. All of the waveforms were modulated with mono-polar chopping with 30 s between waveforms, in kidney phantom. Parameters included d=2 cm, e=3 cm, C=300 μF, and stainless steel needle electrodes with 1.8 mm thickness. Panel G illustrates a waveform having an initial voltage of 2300V, 40 μs DP, 400 μs PP, with a total of 750 DPs. Panels H and I illustrate waveforms having initial voltages of 2000V, 10 μs DP, 400 μs PP, and 3000 total DPs. The scale for all waveforms is one square equals 500V/200 ms. Panels P-R are images showing that no arcing or discharging occurred in the phantom for the waveforms in panels G-I, respectively. All applied waveforms show successful and complete prevention of discharge/plasma formation.

The examples in FIGS. 14A and 14B demonstrate that modulated waveforms may be a useful tool to reduce or prevent violent discharges when multiple high voltage waveforms are applied. This method may safely allow for higher initial voltages, which may potentially make larger ablation volumes and/or faster E2 applications possible.

Example V

According to a third non-limiting example of the present disclosure, the experimental study was carried out in vivo on three 40 kg and two 30 kg breed female pigs with an experimental setting as described in Example II. The treatment was delivered using two electrodes: A 18-gauge stainless steel needle-type electrode with a variable length (1-4 cm exposed treatment length) insulating sheath. Alternatively, a 13-gauge stainless steel needle was tested for the first time. In all cases the electrodes were inserted in the liver and placed under ultrasound-guidance (Hi Vision Preirus Ultrasound device, Hitachi Medical Systems, Germany). The experiment was carried out in an open-surgery setting to maximize the availability of liver lobes. The delivery of E2 waveforms took place through the described electrodes and with the same apparatus as described in Example III. Oscilloscope trace was used to monitor voltage. Organ harvest took place 24 h post treatment. Histological samples were stained with H&E staining and examined under a microscope.

Figure 15:
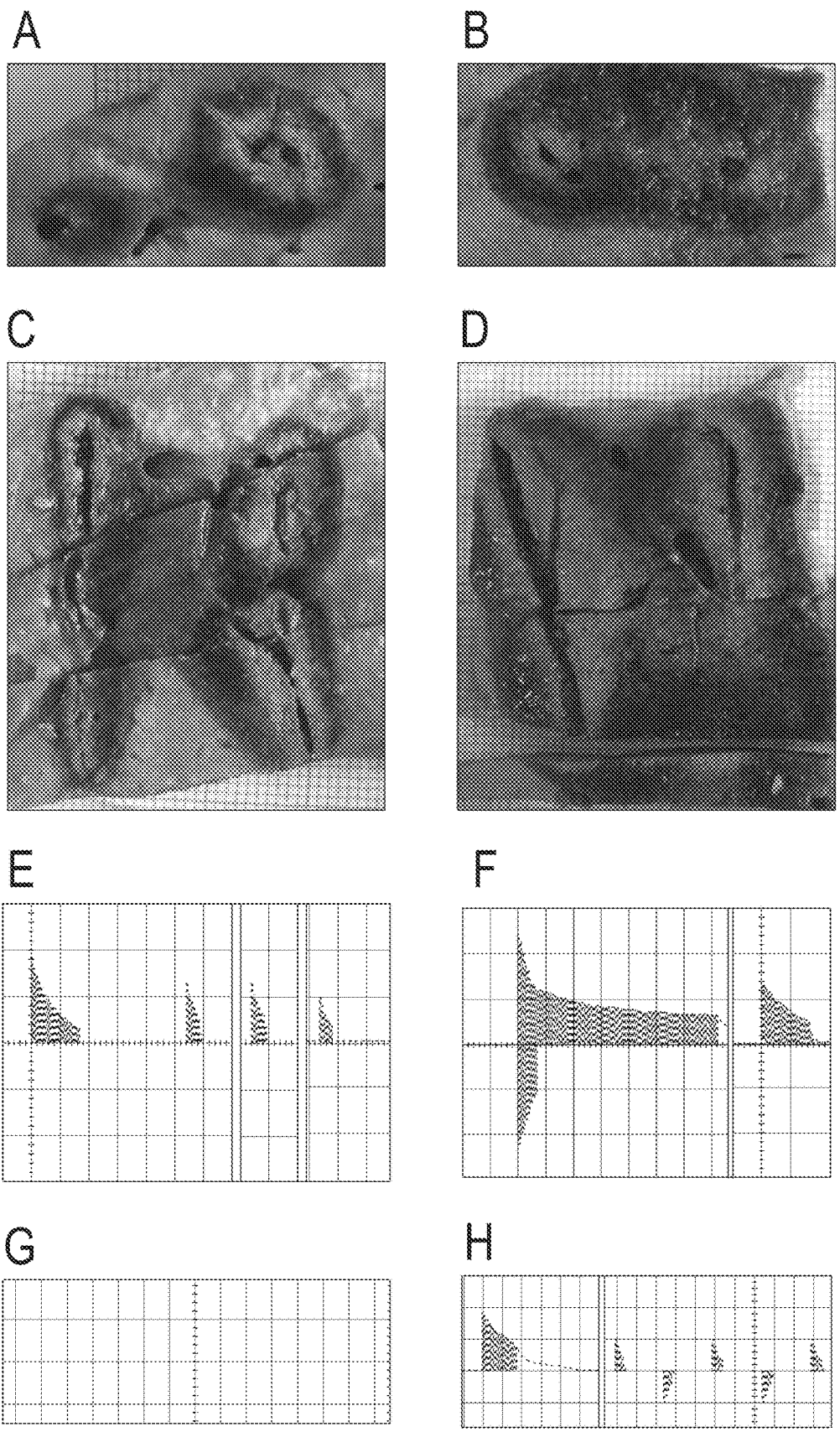
FIG. 15 illustrates the effect of modulated waveforms applied in porcine liver to increase ablation volume according to principles of the present disclosure

FIG. 15 illustrates in vivo E2 treatment with modulated waveforms according to principles of the present disclosure. The modulated waveforms included an initial high voltage waveform and several post waveforms at lower voltages. Application of E2 was in porcine liver with the following parameters: d=2 cm, e=3 cm, C=300 μF, and needle electrodes with 1.8 mm thickness. The scale for all waveforms in FIG. 15 is one square equals 1 kV.

Panel E illustrates a waveform including 10× bi-polar DPs of 80 μs length followed by mono-polar waveform with 2000V peak voltage with 10 μs DP; 800 μs PP followed by two mono-polar waveforms with 1400V peak voltage with 10 μs DP; 400 μs PP followed by a mono-polar post waveform with 1000V peak voltage with 10 μs DP and 400 μs PP. Panel G indicates no further waveforms were applied. Panel A shows a top-view of the gross pathology indicating the region of ablation in the tissue caused by the application of the waveforms in panel E. Panel C shows a side-view of the gross pathology indicating the region of ablation in the tissue caused by application of the waveforms in panel E.

Panel F illustrates a waveform including 160× bi-polar DPs of 80 μs length, followed by a mono-polar waveform with 2300V peak voltage of 10 μs DP; 800 μs PP; followed by a mono-polar waveform with 1600V peak voltage of 10 μs DP; 400 μs PP. Panel H illustrates the waveforms following those illustrated in panel F including a mono-polar waveform with 1400V peak voltage of 10 μs DP; 400 μs PP followed by five mono-polar waveforms with alternating polarities, each with 1000V peak voltages of 10 μs DP, 400 μs PP. Panel B shows a top-view of the gross pathology indicating the region of ablation in the tissue caused by the application of the waveforms in panels F and H. Panel D shows a side-view of the gross pathology indicating the region of ablation in the tissue caused by application of the waveforms in panels F and H.

Figure 16:
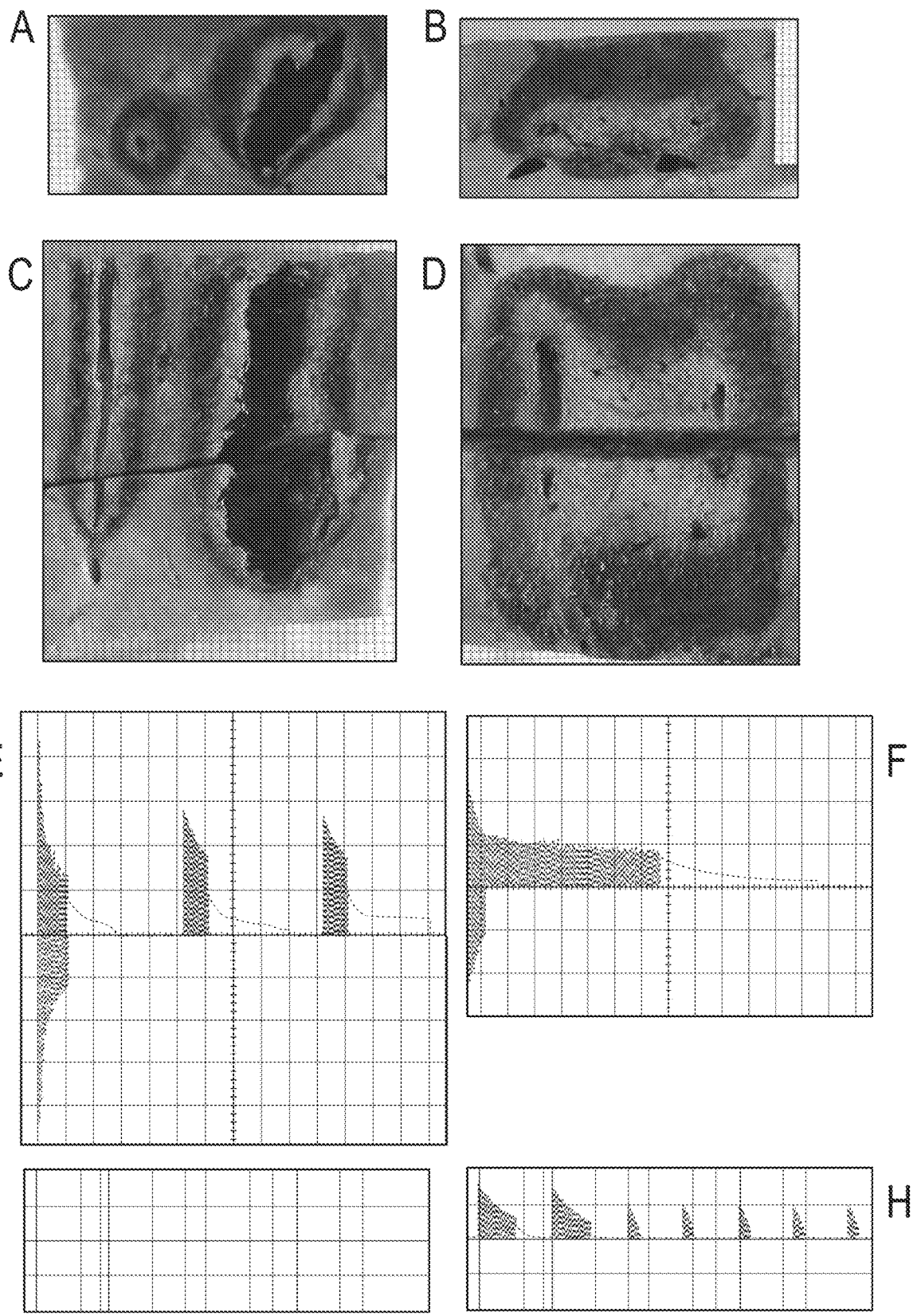
FIG. 16 illustrates the effect of modulated waveforms applied in porcine liver to increase ablation volume according to principles of the present disclosure.

FIG. 16 illustrates in vivo E2 treatment with modulated waveforms according to principles of the present disclosure. The modulated waveforms included an initial high voltage waveform and several post waveforms at low voltage. Application of E2 was in porcine liver with the following parameters: d=2 cm, e=3 cm, C=300 μF, and needle electrodes with 1.8 mm thickness. The scale for all waveforms in FIG. 16 is one square equals 1 kV.

Panel E illustrates a bi-polar waveform with parameters 60 μs high plateau DP, 3×5 μs low plateau DP, 400 μs PP followed by a mono-polar waveform with 1500V peak voltage of 10 μs DP, 400 μs PP followed by a mono-polar waveform with 1400V peak voltage of 10 μs DP, 400 μs PP. Panel G indicates that no further waveforms were applied. Panel A shows a top-view of the gross pathology indicating the region of ablation in the tissue caused by the application of the waveforms in panel E. Panel C shows a side-view of the gross pathology indicating the region of ablation in the tissue caused by application of the waveforms in panel E. This protocol resulted in a lesion size of 34×25×20 mm.

Panel F illustrates a hybrid waveform including a bi-polar high voltage phase (2500V, 10 DPs of 80 μs length) followed by a mono-polar chopping phase. Panel H illustrates the waveforms following the hybrid waveform, including a mono-polar waveform with 1600V peak voltage, 4000 DPs of 10 μs length and 800 μs PP then followed by a mono-polar waveform with 1400V peak voltage, 2000 DPs of 10 μs length and 400 μs PP, and finally followed by five mono-polar waveforms each having 1000V peak voltages, 2000 DPs of 10 μs length and 400 μs PP. Panel B shows a top-view of the gross pathology indicating the region of ablation in the tissue caused by the application of the waveforms in panels F and H. Panel D shows a side-view of the gross pathology indicating the region of ablation in the tissue caused by application of the waveforms in panels F and H. This protocol resulted in a lesion size of 43×36×15 mm.

Figure 17:
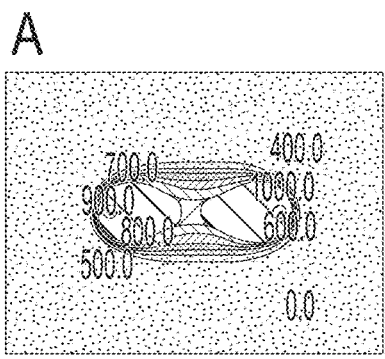
FIG. 17 illustrates the effect of modulated waveforms applied in porcine liver to increase ablation volume according to principles of the present disclosure.
Figure 17:
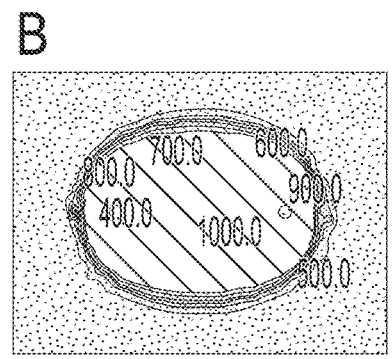
Figure 17:
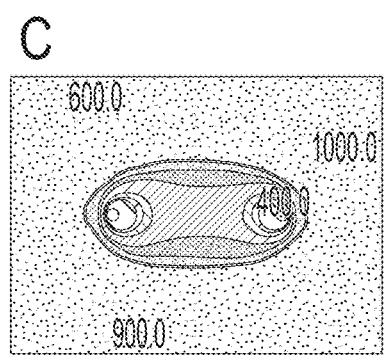
Figure 17:
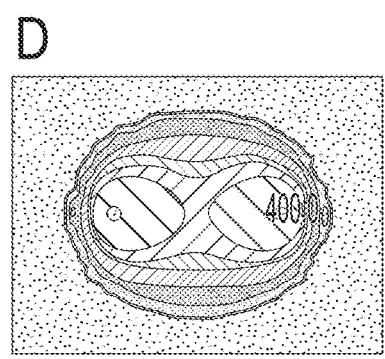
Figure 17:
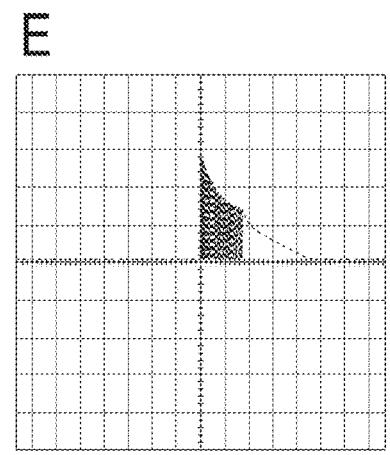
Figure 17:
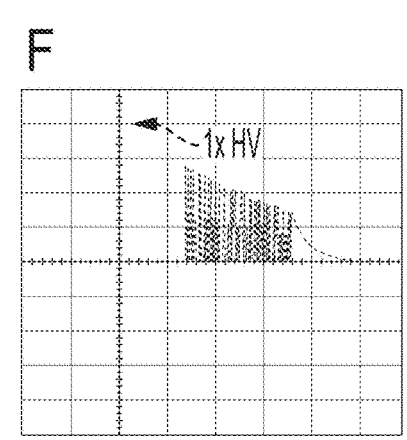
Figure 17:
Figure 17:
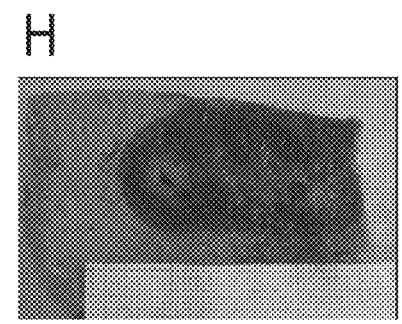

FIG. 17 illustrates a comparison between a single high voltage modulated waveform and a pre-waveform followed by a high voltage modulated waveform according to principles of the present disclosure. Panels A, C, E, and G illustrate the ablation without a high voltage pre-waveform and panels B, D, F, H illustrate ablation with a high voltage pre-waveform. Panels A and B illustrate the electric field strength (V/cm) simulation for the peak voltage (panel A: 1500V, panel B: 2700V). The shaded regions indicate the area where electroporation is likely to take place. Panels C and D show the simulation of current density (A/m^2). The current density illustrates why high voltages may be more prone to arcing, discharges, and/or plasma formations. Panels E and F show oscilloscope readings for the applications of the modulated waveforms in pig liver. The gross pathology of the tissue is shown in panels G and H. This example illustrates that one high voltage waveform may increase the reversible electroporation penumbra and with it the electrolytic electroporation ablation area.

The examples in FIGS. 15-17 demonstrate that modulated waveforms may be feasible and safe in vivo, and may be a useful tool to prevent or reduce violent discharges when multiple high voltage waveforms are applied. This method may safely allow for higher initial voltages, which may make larger ablation volumes and/or faster application of E2 possible.

Example VI

Figure 18:
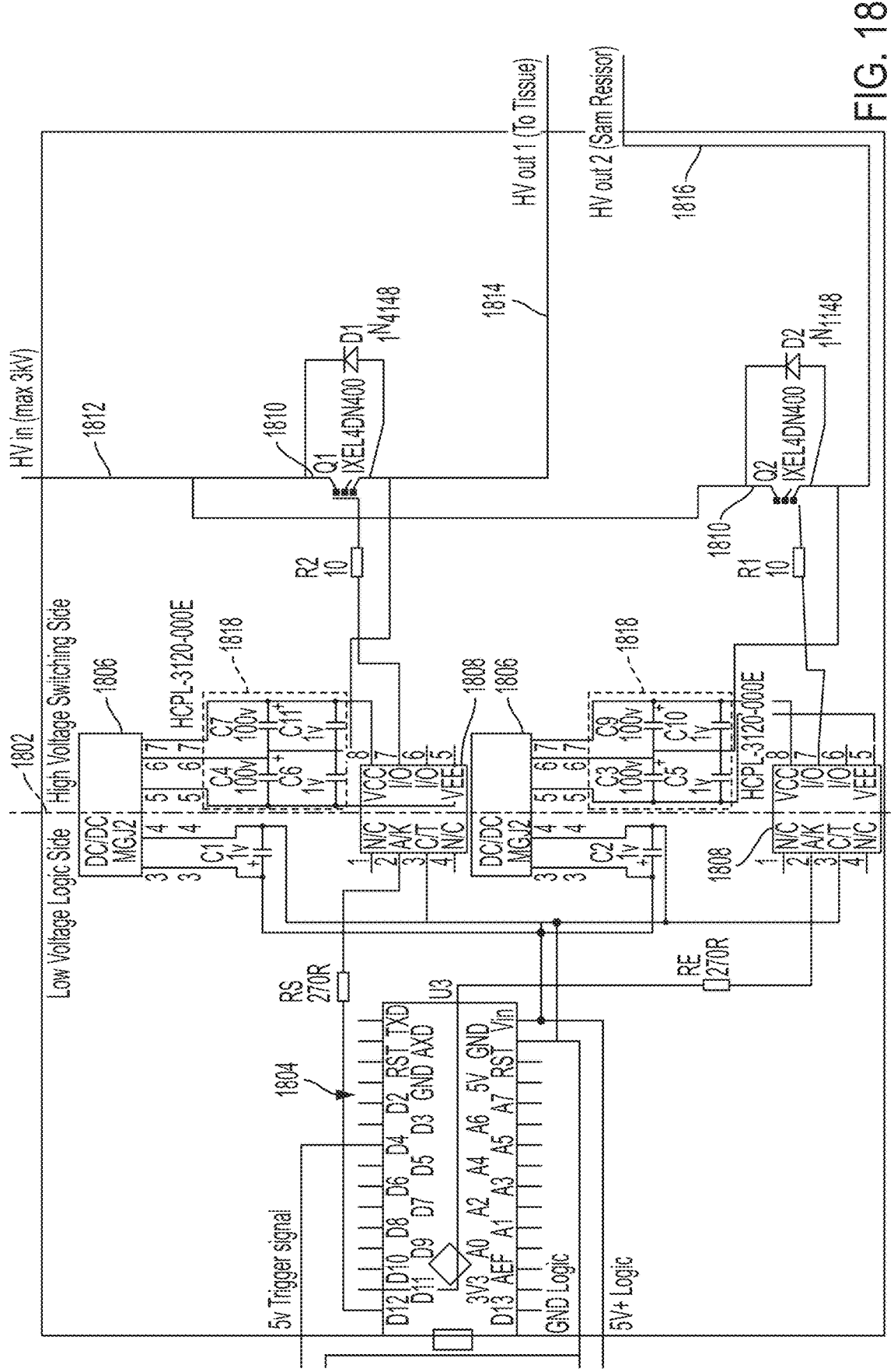
FIG. 18 is a circuit diagram according to principles of the present disclosure.
Figure 19A:
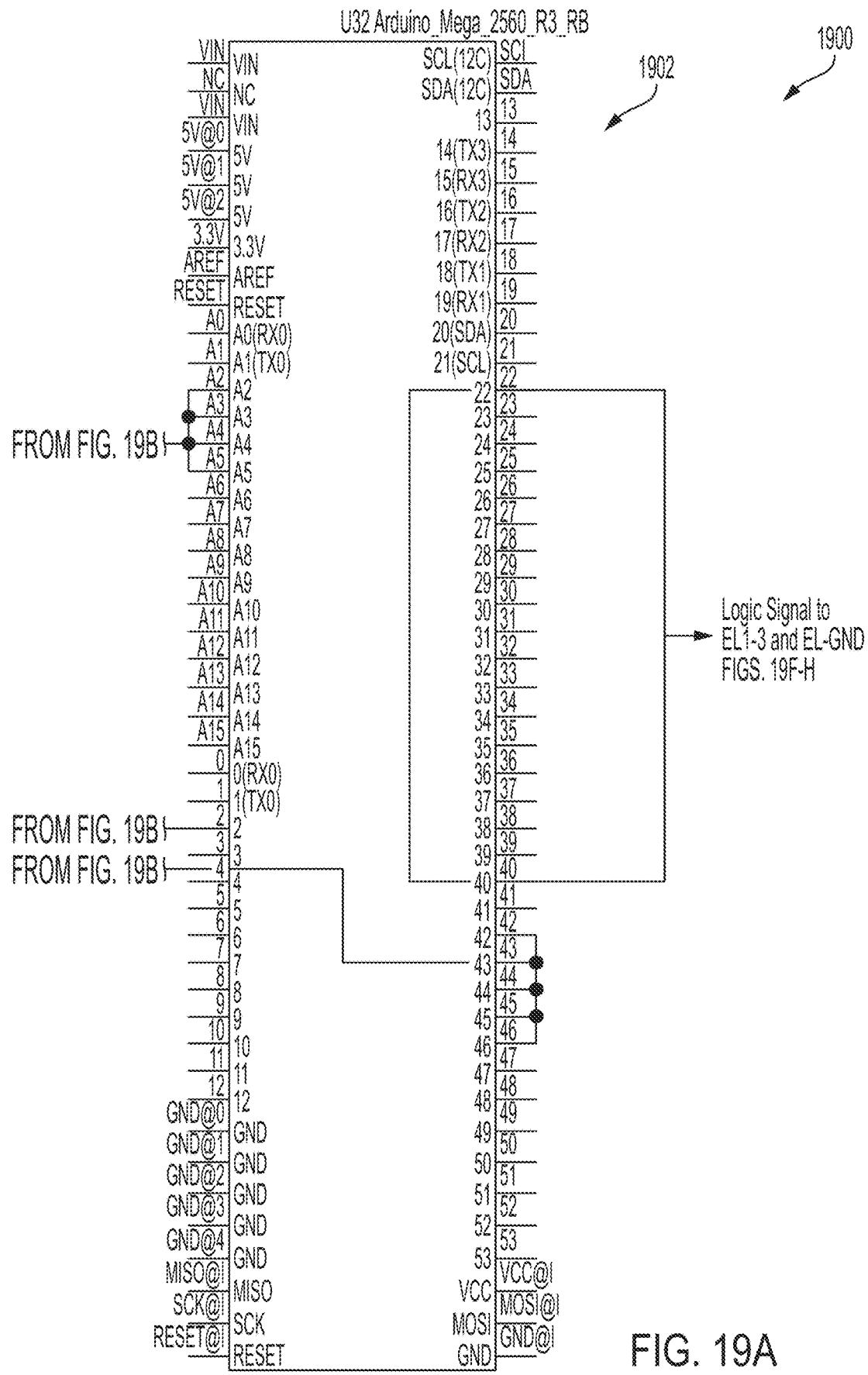
FIGS. 19A-19H are a circuit diagram according to principles of the present disclosure.
Figure 19B:
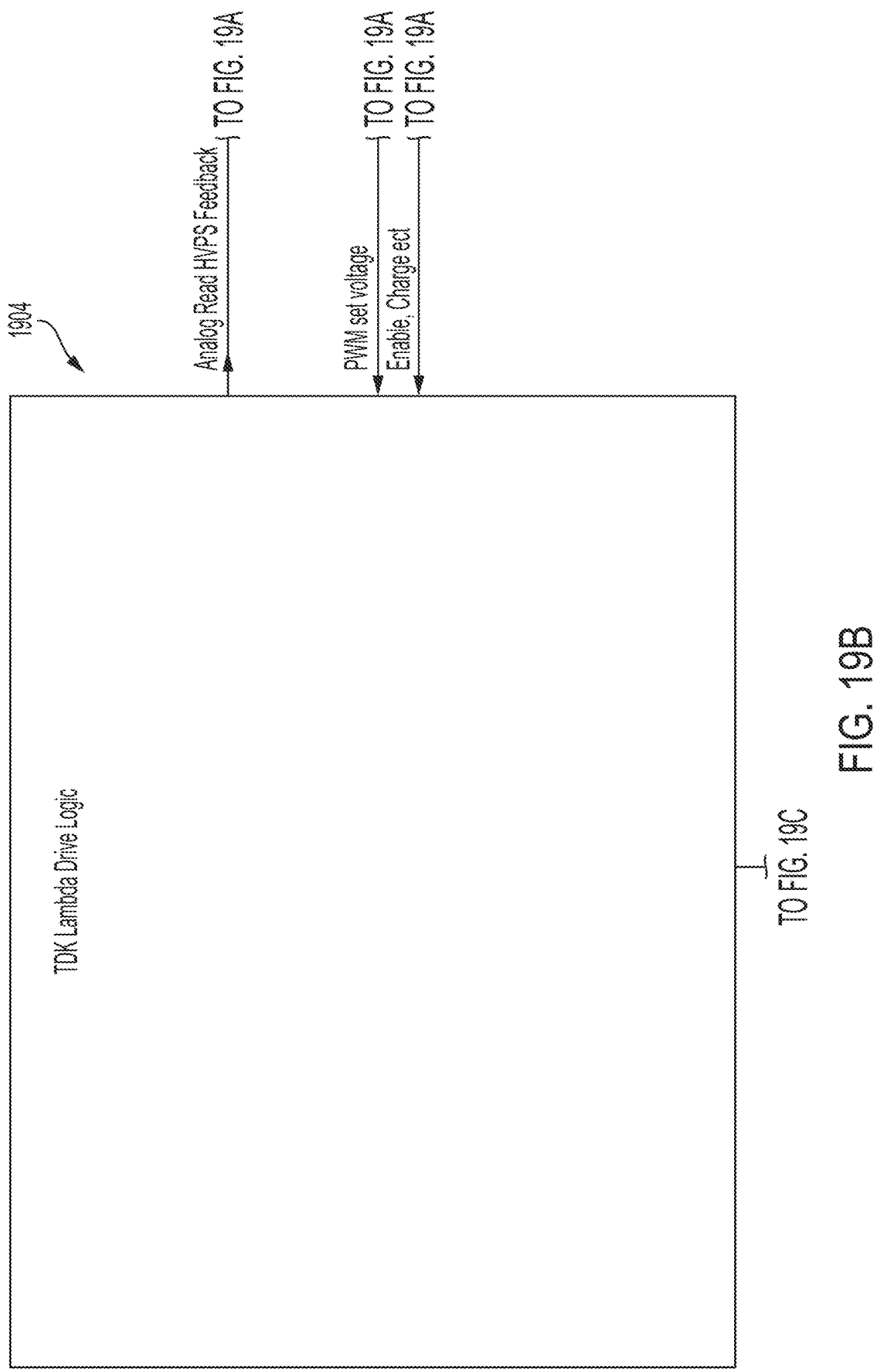
Figure 19C:
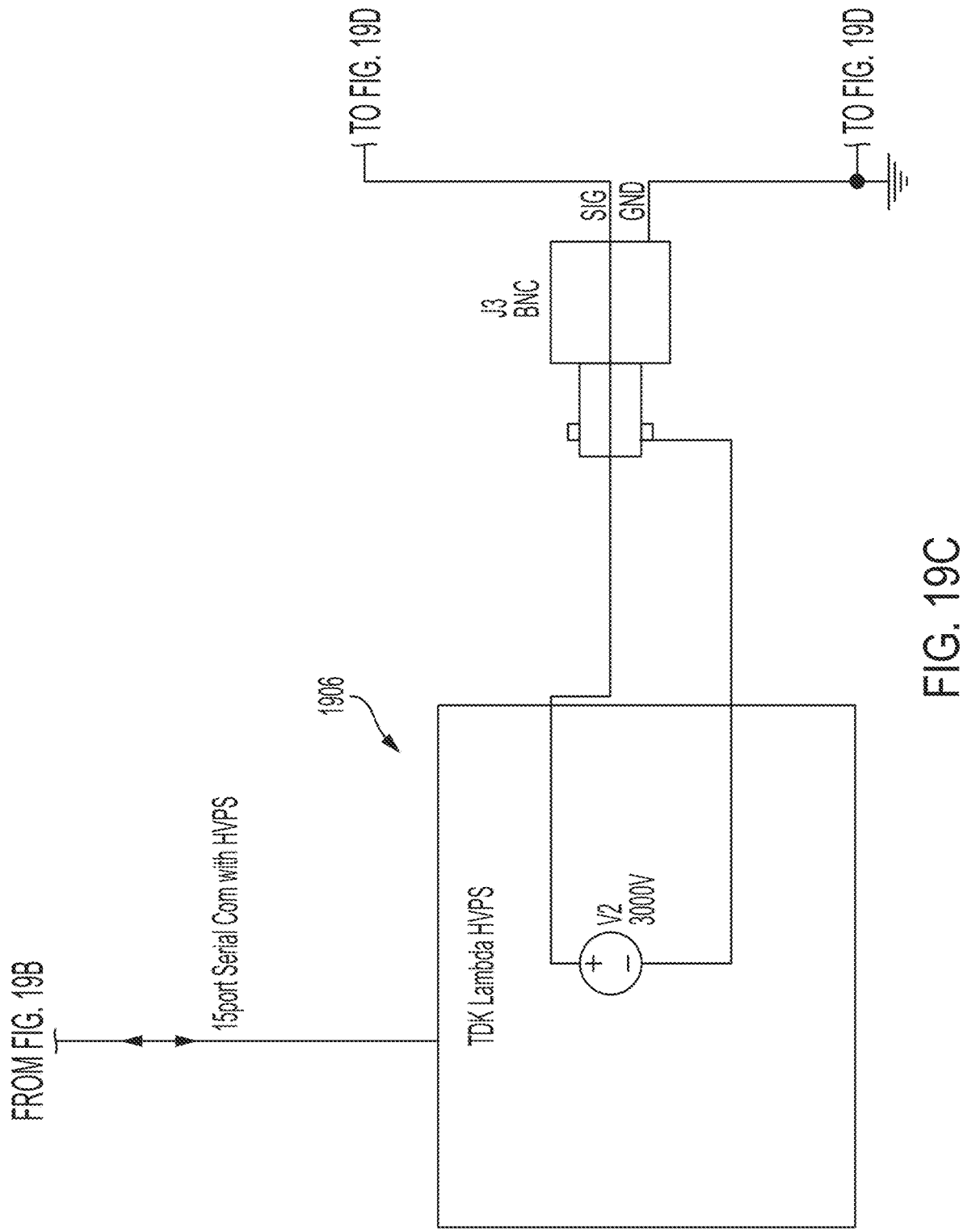
Figure 19D:
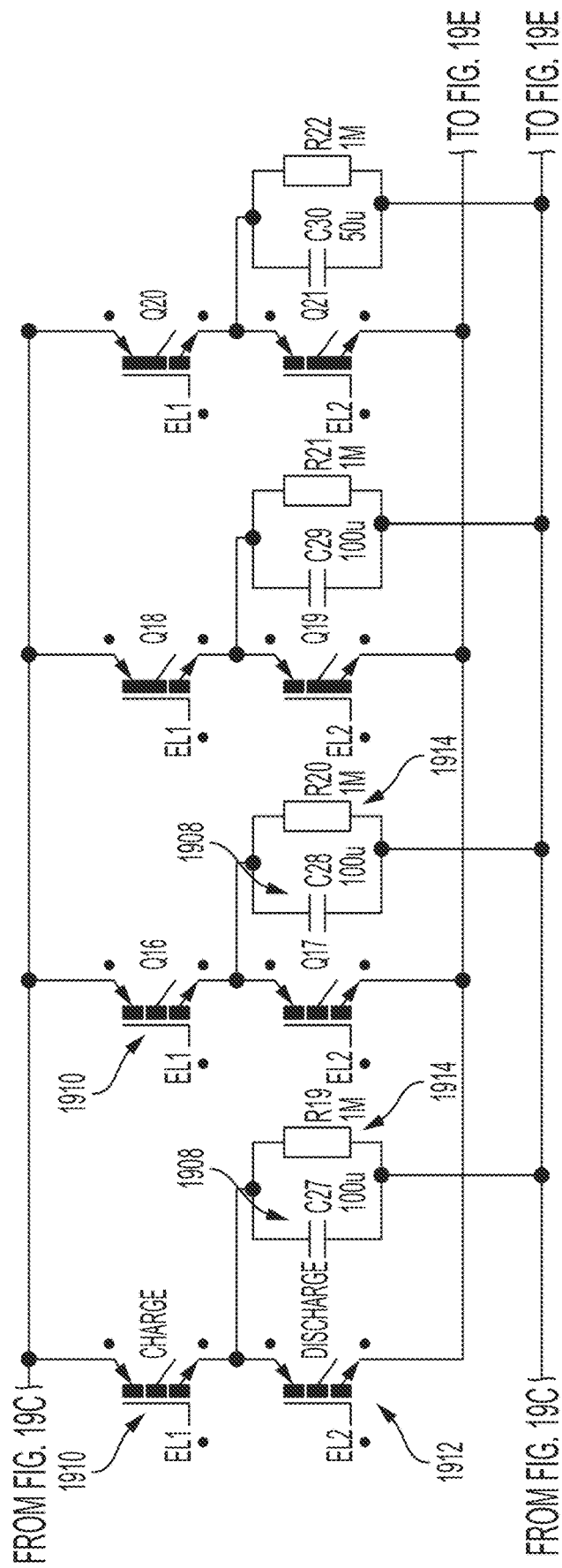
Figure 19E:
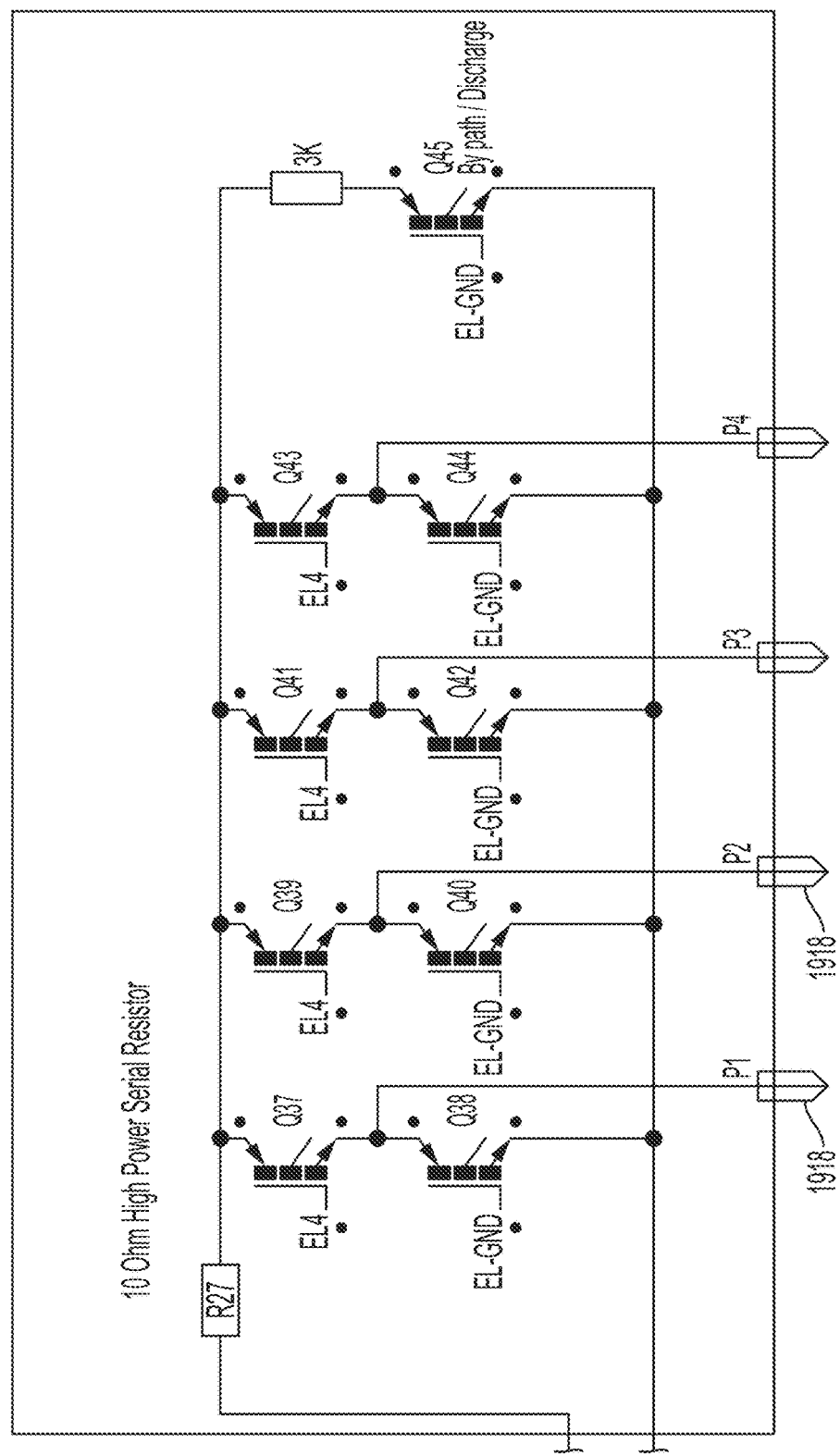
Figure 19F:
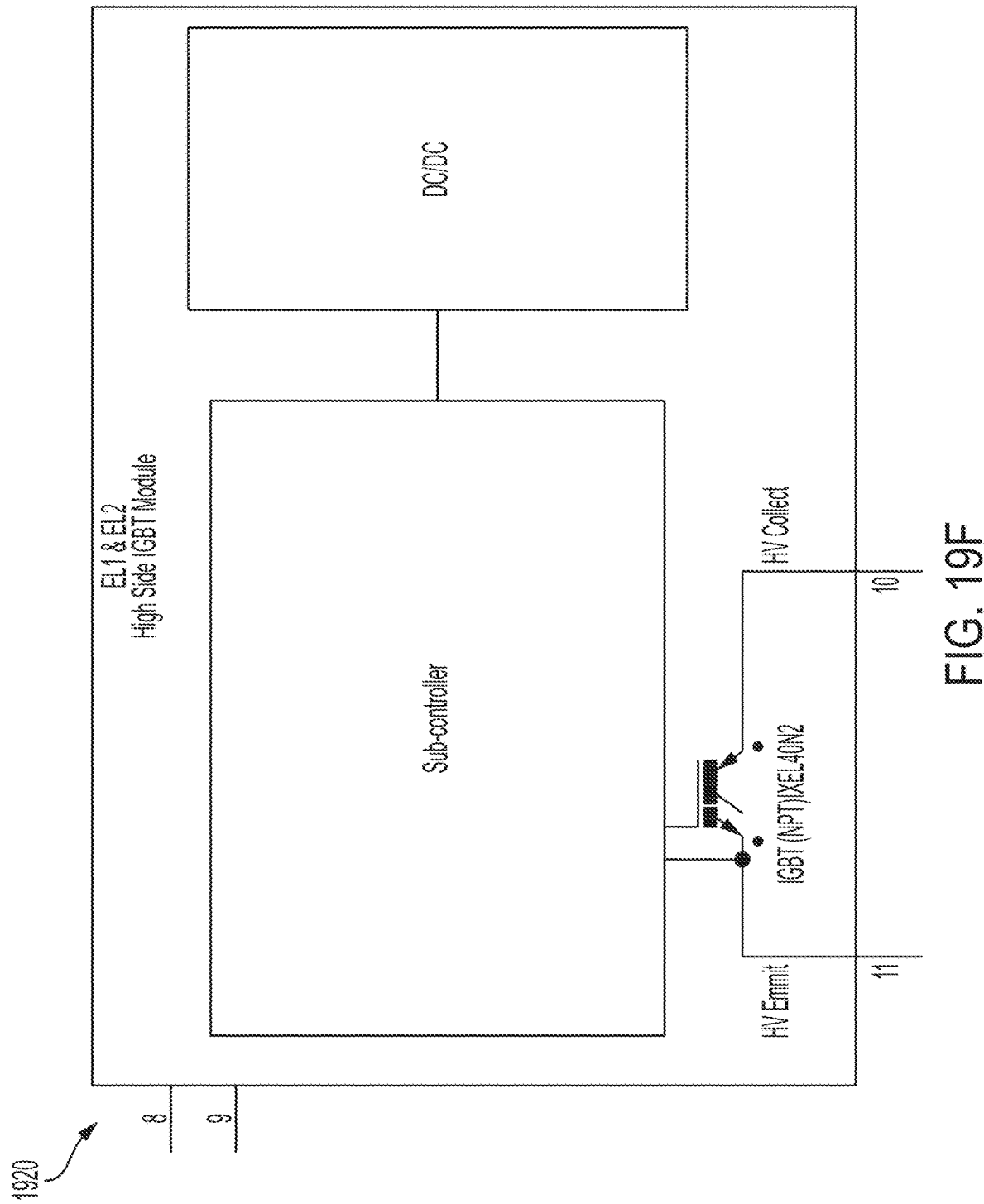
Figure 19G:
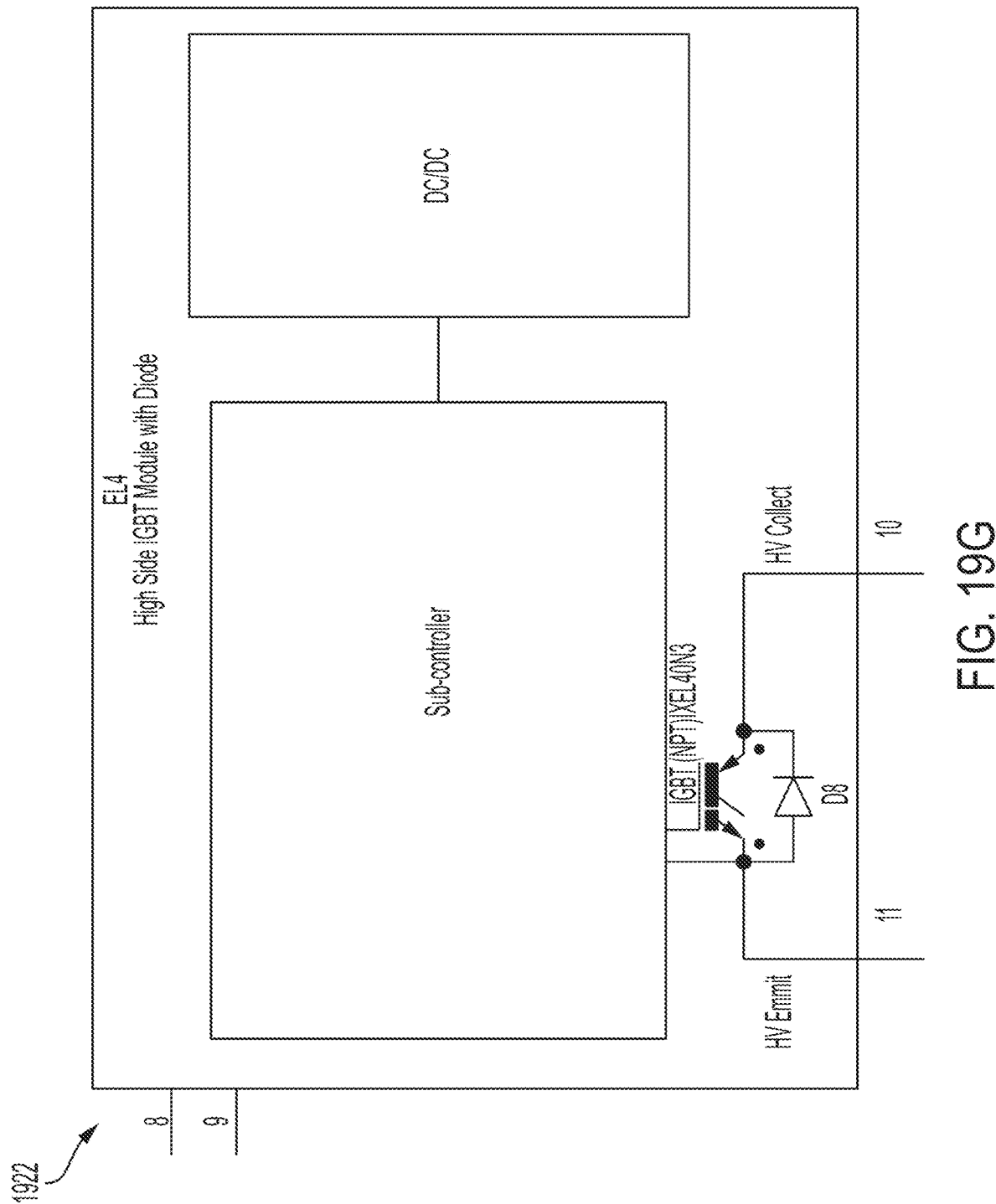
Figure 19H:
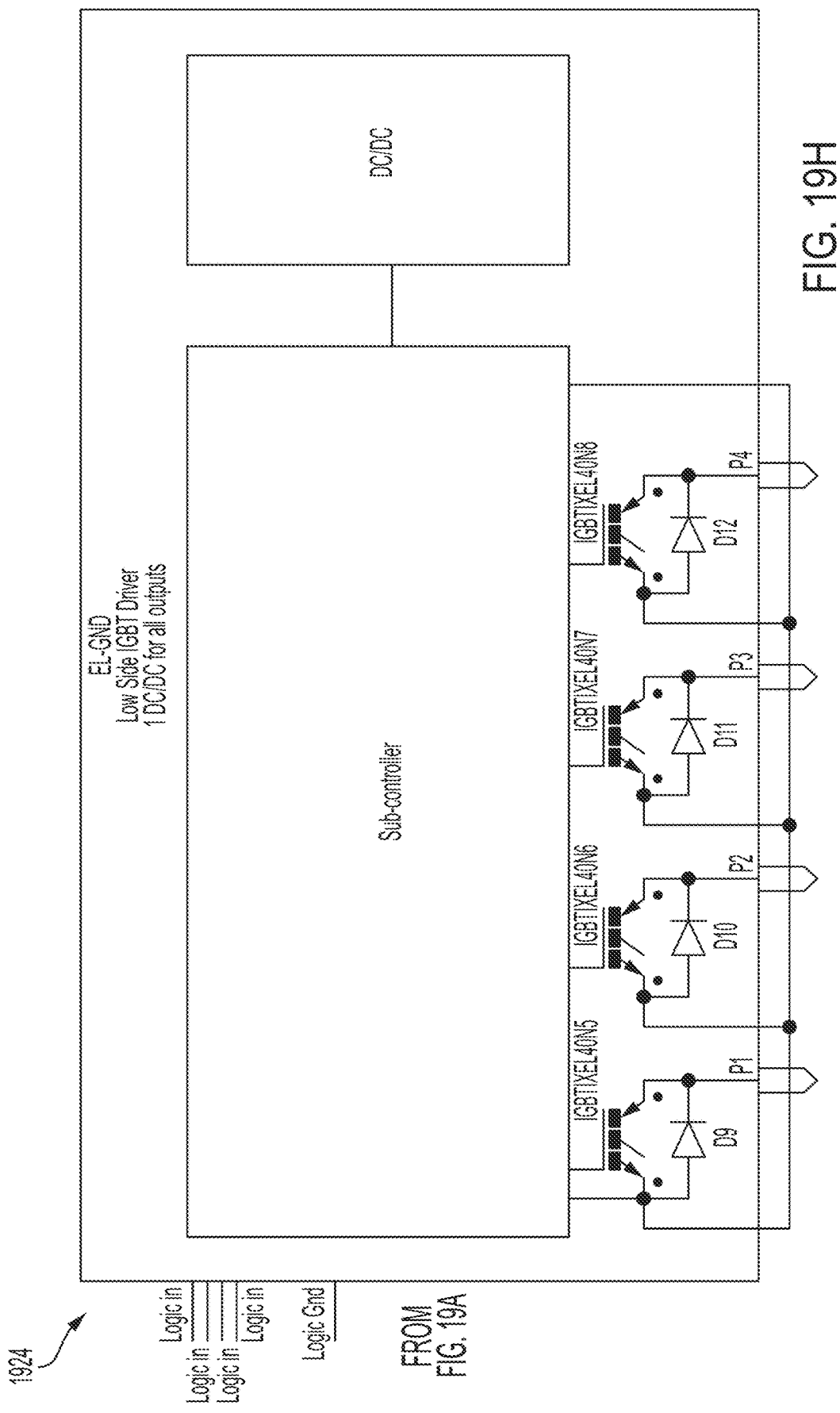

FIG. 18 is a circuit diagram of a circuit 1800 according to principles of the present disclosure. Circuit 1800 may be used to implement at least a portion of the system 200 shown in FIG. 2.

The circuit 1800 may have a low voltage logic side and a high voltage switching side as indicated by dashed line 1802. The low voltage logic side may include a controller 1804 that may be coupled to one or more direct current/direct current (DC/DC) converters 1806 that level shift from the low voltage to the high voltage. The circuit 1800 may further include sub-controllers 1808 configured to receive control signals from the controller 1804. Based on control signals from the controller 1804, the sub-controllers 1808 may provide control signals to control the DC/DC converters 1806 and solid state switches 1810. In some embodiments, the controller 1804 and/or sub controllers 1808 may be included in a controller, such as controller 206. In some embodiments, the DC/DC converters 1806 may be included in a power supply, such as power supply 202. The solid state switches 1810 may selectively couple an ablation target (not shown) in FIG. 18 to a high voltage received from a voltage source (not shown). The high voltage may be received via line 1812 and transmitted to the ablation target via line 1814 and/or line 1816. In some embodiments, line 1812 may be provided from a power supply, such as power supply 202. In some embodiments, line 1814 and/or line 1816 may be coupled to electrodes (not shown). In some embodiments, line 1816 may be coupled to a resistor (not shown). In some embodiments, circuit 1800 may include one or more capacitances 1818, which may be implemented by one or more capacitors. In some embodiments, the capacitances 1818 and/or switches 1810 may be included in a waveform generator, such as waveform generator 204.

Example VII

FIGS. 19A-H are a circuit diagram of a circuit 1900 according to principles of the present disclosure. Circuit 1900 may be used to implement at least a portion of the system 200 shown in FIG. 2. The circuit 1900 may couple up to four electrodes (not shown) to deliver pulses to an ablation target (not shown).

Circuit 1900 may include a controller 1902 (See FIG. 19A) for controlling the various components of the circuit 1900. In the example shown in FIG. 19A, the controller 1902 is an Arduino Mega 2560 controller. The controller 1902 may provide control signals to drive logic 1904 (See FIG. 19B). The drive logic 1904 may control a high voltage power source 1906 (See FIG. 19C). The power source 1906 may provide voltage to charge one or more capacitors 1908 (See FIG. 19D). The power source 1906 may be selectively coupled to the one or more capacitors via switches 1910. The capacitors 1908 may be selectively discharged via switches 1912. In some embodiments, the capacitors may be coupled in parallel with resistors 1914. The capacitors 1908 and resistors 1914 may be selectively coupled to electrode ports 1918 via a plurality of switches of a switch box 1916 (See FIG. 19E). The switches of the switch box 1916 and the switches 1910 and 1912 may be controlled by various driver circuits 1920, 1922, and 1924 (See FIGS. 19F, 19G, and 19H, respectively). The driver circuits 1920, 1922, and 1924 may in turn control the switches based on control signals received from the controller 1902 shown in FIG. 19A.

In some embodiments, the controller 1902, drive logic 1904 and/or drivers 1920, 1922, and/or 1924 may be included in a controller such as controller 206. In some embodiments, the high voltage power source 1906 may be included in a power supply such as power supply 202. In some embodiments, the switches 1910, 1912, capacitors 1908, resistors 1914, and/or switch box 1916 may be included in a waveform generator, such as waveform generator 204.

The examples provided are for explanatory purposes only and should not be considered to limit the scope of the disclosure. For example, shape of waveforms according to the principles of the present disclosure, as well as other factors of the application, may differ depending on the goal that is to be achieved, such as avoidance of discharge, inducing controlled discharge, tissue-dependent cell death, cell-dependent cell death, time-dependent effects of cell death or aiming to produce particular toxic substances during the procedure that will target specific tissue or cells. In another example, a circuit may include more or fewer components depending on a desired number of electrodes. Those skilled in the art will recognize that the examples provided of both the design delivery systems and the clinical applications are not the limit of the uses of the combination of electroporation and electrolysis. Many configurations of delivery systems exist, as well as applications that would benefit from the use of the modulated waveform described herein.

The combined effect of electroporation with electrolysis with modulated waveforms according to the principles of the present disclosure may allow for more effective ablation of tissue, for effective and safe ablation of various types of tissue with varying properties, and/or for faster ablation of higher tissue volumes in some applications.

It is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present devices, apparatuses, systems, and methods and should not be construed as limiting the appended claims to any particular embodiment or group of embodiments. Thus, while the present disclosure has been described in particular detail with reference to exemplary embodiments, it should also be appreciated that numerous modifications and alternative embodiments may be devised by those having ordinary skill in the art without departing from the broader and intended spirit and scope of the present disclosure as set forth in the claims that follow. Accordingly, the specification and drawings are to be regarded in an illustrative manner and are not intended to limit the scope of the appended claims.

What is claimed is:

1. A system comprising:
    a waveform generator configured to generate a waveform comprising at least one of a voltage or a current, the waveform having an exponential decay;
    a controller configured to modulate the waveform generated by the waveform generator to cause electroporation and electrolysis at an ablation target, wherein said modulate comprises interrupting delivery of the at least one of the voltage or the current to the ablation target during the exponential decay; and
    an electrode electrically coupled to the waveform generator and configured to receive the waveform and deliver the at least one of the voltage or the current to the ablation target.

2. The system of claim 1, further comprising a computing device configured to program the controller with a desired modulation of the waveform.

3. The system of claim 1, wherein the controller includes a computing device.

4. The system of claim 1, wherein the controller modulates the waveform by selectively coupling and decoupling the waveform generator from the electrode to interrupt delivery of the at least one of the voltage or the current to the ablation target.

5. The system of claim 1, wherein the controller modulates the waveform by switching a polarity of the at least one of the voltage or the current.

6. The system of claim 1, wherein the waveform includes a decay component and the controller modulates the waveform by adjusting the decay component.

7. The system of claim 1, wherein the controller is further configured to control an initial voltage of the waveform.

8. The system of claim 1, further comprising a sensor in communication with the controller, wherein the sensor is configured to detect a parameter at or in a vicinity of the ablation target, wherein the controller is configured to modulate the waveform based, at least in part, on the parameter.

9. The system of claim 8, wherein the parameter is at least one of a voltage, a current, a temperature, or an impedance.

10. The system of claim 1, wherein the waveform generator comprises:
    a capacitance configured to be charged by a power supply coupled to the waveform generator;
    a resistance coupled to the capacitance and the electrode, wherein the capacitance is configured to discharge through the resistance to the electrode; and
    a switch coupled between the capacitance and the electrode, wherein the switch selectively couples the capacitance to at least one of a discharge bypath or discharge through the electrode, wherein selective coupling of the switch is controlled by the controller.

11. The system of claim 10, wherein the switch is a solid state switch.

12. The system of claim 1 further comprising a plurality of electrodes electrically coupled to the waveform generator and configured to receive the waveform and deliver the at least one of the voltage or the current to the ablation target.

13. A method comprising:
    applying a waveform comprising a pulse of at least one of a voltage or a current to an ablation target, the waveform having an exponential decay, wherein the pulse is configured to cause electroporation and electrolysis at the ablation target; and
    modulating the pulse to intermittently interrupt the at least one of the voltage or the current at the ablation target during the exponential decay.

14. The method of claim 13, wherein modulating the pulse comprises selectively opening and closing a switch.

15. The method of claim 13, wherein the pulse includes a decay component and modulating the pulse alters the decay component of the pulse.

16. The method of claim 13, further comprising modulating the pulse to switch a polarity of the at least one of the voltage or the current.

17. The method of claim 13, wherein modulating the pulse occurs within a time interval of interest of the pulse.

18. The method of claim 13, wherein modulating the pulse to intermittently interrupt the at least one of the voltage or the current at the ablation target is based, at least in part, on:
   a delivery period, wherein the at least one of the voltage or the current is applied during the delivery period, and
   a pause period, wherein the at least one of the voltage or the current is interrupted during the pause period.

19. The method of claim 18, wherein modulating the pulse to intermittently interrupt the at least one of the voltage or the current at the ablation target is further based, at least in part, on a total number of delivery periods.

20. The method of claim 13, further comprising:
   detecting, with a sensor, a parameter in a vicinity of the ablation target; and
   modulating the pulse, based at least in part, on a detected value of the parameter.

* * * * *